(12) United States Patent
Braam

(10) Patent No.: US 12,043,846 B2
(45) Date of Patent: *Jul. 23, 2024

(54) CARDIOMYOCYTES DERIVED FROM PLURIPOTENT MAMMALIAN STEM CELLS

(71) Applicant: Ncardia B.V., Leiden (NL)

(72) Inventor: Stefan Robbert Braam, Leiden (NL)

(73) Assignee: NCARDIA B.V., Leiden (NL)

( * ) Notice: Subject to any disclaimer, the term of this patent is extended or adjusted under 35 U.S.C. 154(b) by 693 days.

This patent is subject to a terminal disclaimer.

(21) Appl. No.: 16/899,121

(22) Filed: Jun. 11, 2020

(65) Prior Publication Data

US 2020/0370018 A1 Nov. 26, 2020

Related U.S. Application Data

(63) Continuation of application No. 14/897,314, filed as application No. PCT/NL2014/050366 on Jun. 6, 2014, now Pat. No. 10,696,947.

(30) Foreign Application Priority Data

Jun. 11, 2013 (NL) ..................................... 2010953

(51) Int. Cl.
C12N 5/077 (2010.01)

(52) U.S. Cl.
CPC ........ *C12N 5/0657* (2013.01); *C12N 2500/25* (2013.01); *C12N 2500/30* (2013.01); *C12N 2500/32* (2013.01); *C12N 2500/33* (2013.01); *C12N 2500/34* (2013.01); *C12N 2500/36* (2013.01); *C12N 2500/38* (2013.01); *C12N 2500/90* (2013.01); *C12N 2501/30* (2013.01); *C12N 2501/33* (2013.01); *C12N 2501/395* (2013.01); *C12N 2501/40* (2013.01); *C12N 2501/998* (2013.01); *C12N 2506/02* (2013.01); *C12N 2506/45* (2013.01)

(58) Field of Classification Search
CPC .............. C12N 5/0657; C12N 2500/25; C12N 2500/30; C12N 2500/32; C12N 2500/33; C12N 2500/34; C12N 2500/36; C12N 2500/38; C12N 2500/90; C12N 2501/30; C12N 2501/33; C12N 2501/395; C12N 2501/40; C12N 2501/998; C12N 2506/02; C12N 2506/45; A61P 43/00

See application file for complete search history.

(56) References Cited

U.S. PATENT DOCUMENTS

| | | | |
|---|---|---|---|
| 5,232,848 A | 8/1993 | Wolfe et al. | |
| 6,221,911 B1 * | 4/2001 | Lavin | A61K 31/425 514/567 |
| 2010/0034785 A1 | 2/2010 | Pedersen et al. | |
| 2010/0064380 A1 | 3/2010 | Pedersen et al. | |
| 2010/0166713 A1 | 7/2010 | Dalton et al. | |
| 2010/0317104 A1 | 12/2010 | Elefanty et al. | |
| 2011/0076253 A1 | 3/2011 | Snyder et al. | |
| 2011/0086379 A1 | 4/2011 | Blak et al. | |
| 2013/0136721 A1 | 5/2013 | Zambidis et al. | |
| 2015/0017718 A1 | 1/2015 | Nakatsuji et al. | |

FOREIGN PATENT DOCUMENTS

| | | | |
|---|---|---|---|
| CN | 1995334 A | 7/2007 | |
| JP | 2007124982 A | 5/2007 | |
| JP | 2007228815 A | 9/2007 | |
| WO | 90/03430 | 4/1990 | |
| WO | 2003/006950 A2 | 1/2003 | |
| WO | 03/064598 A2 | 8/2003 | |
| WO | 2004000993 A2 | 12/2003 | |
| WO | 2004/098490 A2 | 11/2004 | |
| WO | 2007016366 A2 | 2/2007 | |
| WO | 2008056166 A2 | 5/2008 | |
| WO | 2008056173 A2 | 5/2008 | |
| WO | 2008/088863 A2 | 7/2008 | |
| WO | 2008112323 A1 | 9/2008 | |
| WO | 2010007031 A2 | 1/2010 | |
| WO | 2011058558 A2 | 5/2011 | |
| WO | 2012/143407 A1 | 10/2012 | |
| WO | 2013/019661 A1 | 2/2013 | |
| WO | WO-2013019661 A1 * | 2/2013 | ........... C12N 5/0657 |
| WO | 2014/200339 A1 | 12/2014 | |

OTHER PUBLICATIONS

Passier et al., "Increased Cardiomyocyte Differentiation from Human Embryonic Stem Cells in Serum-Free Cultures", Stem Cells, Jan. 1, 2005; 23:772-780.
Lee, et al., "Triiodothyronine Promotes Cardiac Differentiation and Maturation of Embryonic Stem Cells via the :;lassical Genomic Pathway", Mol Endocrinal, Sep. 2010, 24(9):1728-1736.
Novak-Giese, S., International Search Report from PCT/NL2014/050366, Jul. 29, 2014, 3 pages.
Chattergoon et al., "Thyroid hormone drives fetal cardiomyocyte maturation", FASEB Journal, vol. 26, pp. 397-408. (Year: 2012).
Wang, et al., "Defined media optimization for in vitro culture of bovine somatic cell nuclear transfer {SCNT) embryos", heriogenology 78 (2012) 2110-2119.

(Continued)

*Primary Examiner* — Aaron J Kosar

(74) *Attorney, Agent, or Firm* — BROWDY AND NEIMARK, PLLC

(57) ABSTRACT

The current disclosure relates to a culture medium, different methods to generate adult-like cardiomyocytes from pluripotent embryonic stem cells (ESC) and/or (induced) pluripotent stem cells (iPSC) using the medium, in particular from stem cells that differentiated into (foetal) cardiomyocytes, and to kits comprising the medium, or the medium together with differentiated (foetal) cardiomyocytes derived from pluripotent embryonic stem cells (ESC) and/or (induced) pluripotent stem cells (iPSC).

43 Claims, 4 Drawing Sheets

(56) References Cited

OTHER PUBLICATIONS

Figure 1:
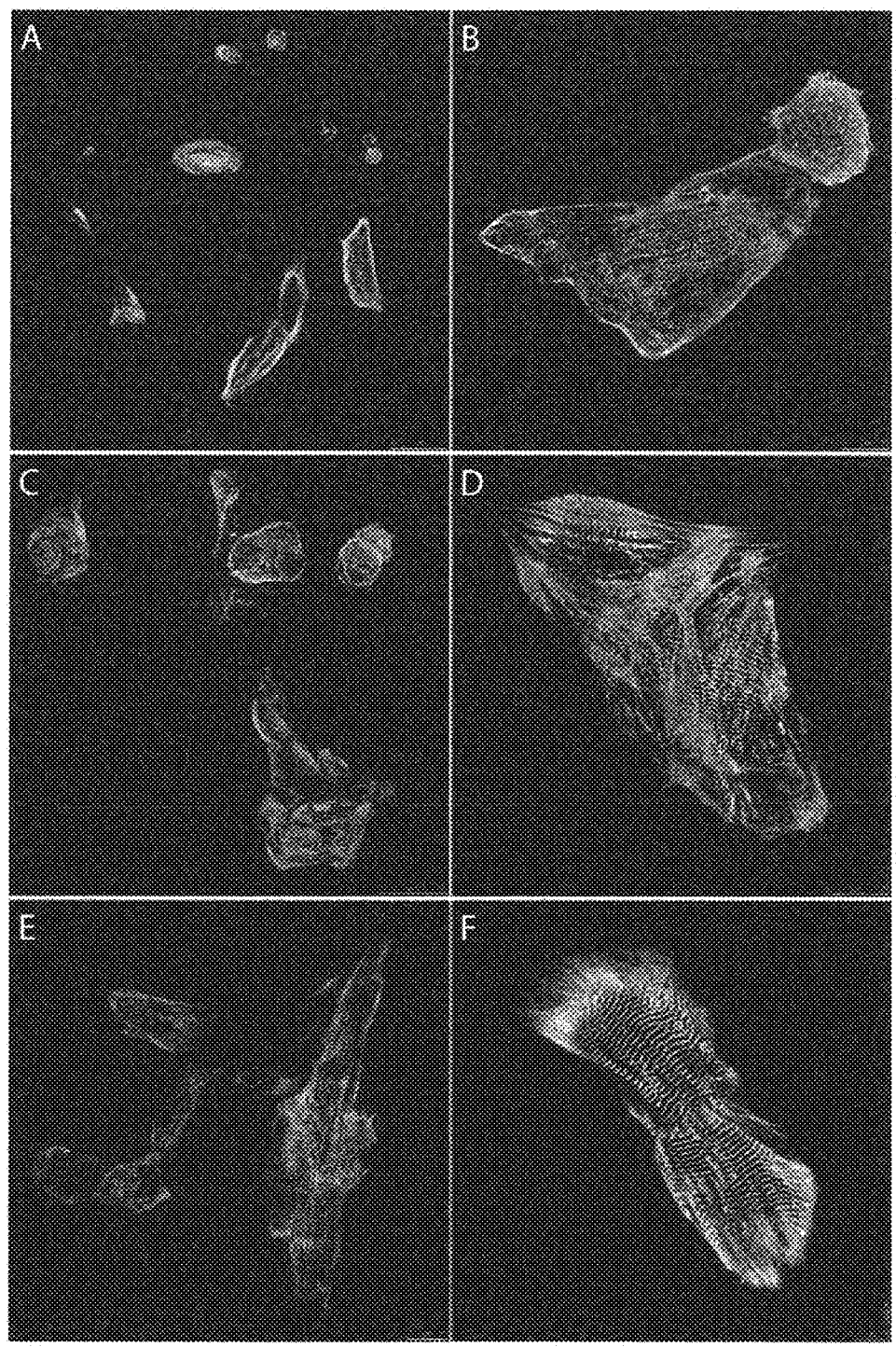

11905—"Chemically Defined Lipid Concentrate", https://www.thermofisher.com/jp/ja/home/lechincal-resources/media-0 . . . 2017.

Mordwinkin, N et al., "A Review of Human Pluripotent Stem Cell-Derived Cardiomyoctyes for High-Throughput Drug Discovery, Cardiotoxicity Screening and Publication Standards", Journals of Cardiovascular Translational Research, vol. 5 (1) 22-30, 2015.

Chung, Y,. et al. "Human Embryonic Stem Cell Lines Generated without Embryo Destruction", Stem Cell Lines, vol. 2 (2): 113-117, 2008.

Burridge, P., : Production of De Novo Cardiomyocytes", Human Pluripotent Stem Cell Differentation and Direct Repogramming" Cell Stem Cell, vol. 10(1): 16-28. 2012.

Kehat, I et al., "Human embryonic stem cell can differentiate into myocytes with structural and functional properties of cardiomyocytes", Journal of Clinical Investigation, vol. 108, 407-414, 2001.

Mummery, C et al., Differentation of Human Embryonic Stem Cells to Cardiomyocytes—Role of Coculture With Visceral Endoderm-llke Cells, Hubrecht Laboratory, 2003, pp. 2733-2740.

Laflamme, M et al., "Cardiomyocytes derived from human embryonic stem cells in pro-survival factors enhance function of infarcted rat hearts", Nature Biotechnology, vol. 25, 1015-1024, 2007.

Dambrot, C., "Strategies for rapidly mapping proviral integration sites and assessing cardiogenic potential of nascent human induced pluripotent stem cell clones", Experimental Cell Research, 327, 297-305, 2015.

Bellin, M., "Isogenic human pluripotent stem cell paris reveal the role of KCNH2 mutation in long-QT sydrome", EMBO, vol. 32, pp. 3161-3175, 2013.

Chattergoon et al., Thyroid hormone inhibits proliferation of fetal cardiac myocytes in vitro, Journal of Endocrinology, 192:R1-R8 (2007).

Yang et al., Tri-iodo-L-thyronine Promotes the Maturation of Human Cardiomyocytes-Derived from Induced Pluripotent Stem Cells, J Mol Cell Cardiol. 72:296-304 (2014).

* cited by examiner

C

CARDIOMYOCYTES DERIVED FROM PLURIPOTENT MAMMALIAN STEM CELLS

FIELD OF THE INVENTION

The present invention generally relates to the field of cell culture and stem cell biology. More specifically, the present invention relates to maturation of foetal-like (immature) cardiomyocytes derived from pluripotent embryonic stem cell (PESC). Particularly, the present invention provides chemically-defined compositions and methods for generating adult-like cardiomyocytes from mammalian PESC-derived foetal-like (immature) cardiomyocytes in vitro. In certain aspects of the invention, methods are provided using the chemically-defined compositions of the invention for generating adult-like cardiomyocytes from foetal-like (immature) cardiomyocytes derived from mammalian PESC in vitro. The chemically-defined culture medium compositions, the generated adult-like cardiomyocytes, and methods of the invention find applications in the fields of drug discovery, drug-induced cardiotoxicity assays, predictive toxicology screening assays, preclinical screening of candidate drugs, cardiovascular research and cardiac disease modelling, regenerative medicine and other applications aimed to model or treat cardiac conditions in adults.

BACKGROUND OF THE INVENTION

Progress in several areas of medicine (i.e. mental health, cardiology, immunity etc.), where new and more effective drugs are needed, is severely impeded by the extreme cost engendered by undesired drug-induced adverse effects associated with several candidate lead compounds in the drug discovery pipeline. One major drawback of the current drug discovery process, for all drug development, is the high rate of attrition of lead compounds caused by unforeseen adverse drug effects, notably cardiotoxic effects, often detected in the later rather than in the earlier phases of the drug discovery pipeline. The prevention of drug-Induced cardiotoxicity, which may manifest itself as cardiac arrhythmias, represents the highest priority for regulatory agencies and (bio)pharmaceutical companies, since manifestation of this type of toxicity is immediately life-threatening. It has been shown that 33% of adverse safety events in clinical studies are generally attributed to cardiac arrhythmic effects, which may lead to sudden death or severe cardiac complications in subjects (Mordwinkin et al (2013) Journal of cardiovascular translational research, Vol: 6(1):22-30).

Therefore, there is an urgent need for new cost-effective strategies to improve the traditional process of drug development/discovery, e.g. eliminate drug-induced cardiotoxic effects. Particularly, there is an urgent unmet need for predicting drug-induced cardiotoxicity at an early stage in the drug pipeline development. Over the last decade, considerable research efforts have been devoted towards this goal. For instance, several biological models and tools have been developed including the use of pluripotent stem cells, ion-channel assays, and computational tools. Particularly, the use of cardiomyocytes derived from pluripotent stem cells is a current focus of interest in the development of innovative predictive assays to rectify the issues relating to cardiotoxicity during drug development.

Pluripotent stem cells, such as pluripotent embryonic stem cells (PESC) and induced pluripotent stem cells (iPSC), are a potential source of cells for generating cardiomyocytes in in vitro culture. The use of cardiomyocytes is not only important for the development of assays for predicting drug-Induced toxicity for all drugs in development, but is also important for cardiac research as well as for the development of new cardiac drugs in general, where cardiomyocytes can be used to uncover new drug targets and assess cardiac drug safety. The ability to produce cardiomyocytes from PESC and/or iPSC in vitro also opens other therapeutic avenues such as regenerative medicine, where PESC- and/or iPSC-derived cardiomyocytes can be used to directly repair damaged cardiac tissues in patents in need thereof, for instance.

The ability to use cardiomyocytes in drug development/discovery, drug safety assay, cardiac disease modelling, cardiac research, regenerative medicine and other biological purposes largely depends on the ability to cultivate and obtain cardiomyocytes derived from PESC and/or iPSC in culture in vitro, which must meet certain phenotypic requirements such as, for instance, a certain level of functional properties (e.g. adult-like electrophysiological patterns) and/or genetic profile (e.g. adult-like expression of cellular fate-specific genetic markers), and/or morphological aspects. (e.g. adult-like shape and histological properties).

In this respect, a main limitation of the art is that current methods and culture medium compositions for generating cardiomyocytes from PESC and/or iPSC in in vitro culture yield results which are suboptimal and do not or only in part match the requirements for applications such as drug development/discovery, drug safety assay, cardiac disease modelling, cardiac research, regenerative medicine, where cardiomyocytes suitable for 'real-life' context (i.e. adult-like state) are needed. That is because current methods and culture medium compositions yield immature cardiomyocytes, which are akin to foetal (foetal-like) cardiomyocytes. Such cardiomyocytes are inadequate for use in applications such as drug development/discovery, drug safety assay, cardiac disease modelling, cardiac research, regenerative medicine and other purposes aimed to model or treat cardiac conditions that typically occur in adulthood and not at earlier developmental stages. Hence, adult-like (mature) cardiomyocytes are better suited than immature cardiomyocytes or foetal-like cardiomyocytes for these purposes.

Therefore, there is a need for improved methods and culture medium compositions for generating adult-like cardiomyocytes (as opposed to immature cardiomyocytes) from PESC and/or iPSC in in vitro culture. There is also a need for improved methods and culture medium compositions to produce larger amount (greater yield) of adult-like cardiomyocytes derived from foetal-like (immature) cardiomyocytes, which are themselves derived from PESC and/or iPSC in in vitro differentiation of the stem cells.

It is an object of the present invention to overcome the major limitations of the art by providing chemically-defined culture medium compositions that promote maturation of foetal-like (immature) cardiomyocytes, which are themselves derived from pluripotent embryonic stem cells in in vitro culture and methods for generating said adult-like cardiomyocytes in in vitro culture, which are more efficient and support larger scale production of adult-like cardiomyocytes that meet the general requirements for cardiac research and clinical applications.

DETAILED DESCRIPTION OF THE INVENTION

General Definition

In the following description and examples, a number of terms are used. In order to provide a clear and consistent understanding of the specification and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

The term 'stem cells' as used herein refers to undifferentiated cells defined by their ability at the single cell level to both self-renew and differentiate to produce progeny cells, including self-renewing progenitors, non-renewing progenitors, and terminally differentiated cells. Stem cells have the ability to divide for indefinite periods in culture. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts. Stem cells are categorized as somatic (adult) stem cells or embryonic stem cells. A somatic stem cell is an undifferentiated cell found in a differentiated tissue that can renew itself (clonal) and (with certain limitations) differentiate to yield all the specialized cell types of the tissue from which it originated.

The term 'embryonic stem cells', In the art also abbreviated as 'ES cells' or ESC (or if of human origin 'hES cells' or 'hESCs') as used herein is generally understood by the skilled person and refers to pluripotent embryonic stem cells (PESC) that are derived from the inner cell mass of a blastocyst. The skilled person understands how to obtain such embryonic stem cells, for example as described by Chung (Chung et al (2008) Stem Cell Lines, Vol 2(2):113-117), which employs a technique that does not cause the destruction of the donor embryo(s).

The term "pluripotency" as used herein is generally understood by the skilled person and refers to an attribute of a pluripotent stem cell that has the potential to differentiate into all cells constituting one or more tissues or organs, for example, any of the three germ layers: endoderm (e.g. Interior stomach lining, gastrointestinal tract, the lungs), mesoderm (e.g. heart, muscle, bone, blood, urogenital tract), or ectoderm (e.g. epidermal tissues and nervous system).

The term 'pluripotent embryonic stem cells', which is abbreviated 'PESC', as used herein refers to pluripotent stem cells derived from early embryos. PESC can differentiate into cells derived from any of the three germ layers. PESC can be distinguished from other types of cells by the use of markers or lineage-specific markers including, but not limited to, Oct-4, Nanog, GCTM-2, SSEA3, and SSEA4.

The term 'Induced pluripotent stem cells', commonly abbreviated as iPSC, as used herein refers to somatic (adult) cells reprogrammed to enter an embryonic stem cell-like state by being forced to express factors important for maintaining the "stemness" of embryonic stem cells. Typically, iPSC are artificially prepared from a non-pluripotent cell, (i.e. adult somatic cell, or terminally differentiated cell) such as fibroblast, a hematopoietic cell, a myocyte, a neuron, an epidermal cell, or the like, by introducing into or otherwise contacting the cell with reprogramming factors. The term "induced pluripotent stem cells (iPSC)" does not include embryonic stem cells.

The term 'thyroid hormone-like compounds' as used herein refers to thyroid hormone (also referred to as triiodothyronine (T3)) as well as to compounds which are analogue to the thyroid hormone T3 or mimic thyroid hormone T3's actions. Non-limiting examples of thyroid hormone-like compounds include thyroid hormone receptor agonist compounds such as DITPA (also referred to as 3,5-diiodothyroproprionic acid or DITPA), GC-1 compounds (which is a thyroid hormone receptor subtype beta (TRbeta) selective agonist from Bristol-Myers Squibb), RO compounds (which is a thyroid hormone receptor subtype beta 1 (TRbeta) selective agonist from Roche Pharmaceuticals), CO23 compound (which is a thyroid hormone subtype alpha 1 (TRalpha1) selective agonist from KaroBio), KB2115 (which is a thyroid hormone receptor subtype beta (THbeta) selective agonist from KaroBio).

In the present invention, the term 'proliferation' or 'multiplication' or 'expansion' as used herein refers to a biological process wherein one PESC or a iPSC (the 'mother cell') grows and divides to produce two PESC or two iPSC cells ('daughter cells') and so on in an exponential process under control conditions in in vitro culture. During the process of PESC or iPSC proliferation or expansion or multiplication, it is understood that a PESC or a iPSC is self-renewing. Self-renewal of a cell is the ability of a given cell to go through numerous cycles of cell division while maintaining an undifferentiated state.

In the present invention, the term 'differentiation' as used herein refers to a biological process whereby an unspecialized PESC or iPSC acquires the features of a specialized cell such as a heart cell (e.g. cardiomyocyte), liver cell, or muscle cell under controlled conditions in in vitro culture. Differentiation is controlled by the interaction of a cell's genes with the physical and chemical conditions outside the cell, usually through signalling pathways involving proteins embedded in the cell surface. In certain embodiments, pluripotent stem cells (e.g. PESC or iPSC) can be exposed to the culture medium compositions and methods of the invention so as to promote differentiation of pluripotent stem cells into foetal-like cardiomyocytes. Cardiac differentiation can be detected by the use of markers selected from, but not limited to, NKX2-5, GATA4, myosin heavy chain, myosin light chain, alpha-actinin, troponin, and tropomyosin (Burridge et al (2012) Stem Cell Cell, Vol. 10(1):16-28, US2013/0029368).

The skilled person is aware of various methods to obtain stem cell, e.g. PESC- and/or iPSC), derived cardiomyocytes. When stem cells are removed from differentiation suppression conditions and/or when grown in suspension aggregates, called embryoid bodies, spontaneous differentiation to cells of the three germ layers occurs. Cardiomyocytes originate from the mesodermal germ layer and differentiation of stem cells into cardiomyocytes thus requires efficient differentiation toward the mesodermal lineage. Such directed differentiation toward the cardiac lineage is mainly achieved by several strategies, including the formation of embryoid bodies in the presence of growth factors and repressors known to influence heart development (see, for example Kehat et al. Clin. Invest. 2001; 108, 407-414), reliance on the influence of endoderm on cardiac differentiation during embryogenesis (Mummery et al., Circulation. 2003; 107, 2733-2740), for example by co-culture of stem cells with mouse END-2 in order to obtain stem-cell derived cardiomyocytes, or by using monolayer culture at high density of stem cells seeded on Matrigel with sequential treatment with activin A and BMP4 (Laflamme et al. 2007; Nat. Biotechnol. 25, 1015-1024).

The term 'undifferentiated' as used herein refers to a PESC and/or iPSC, which has not developed a characteristic of a more specialized cell. As will be recognized by one of skill in the art, the terms "undifferentiated" and "differentiated" are relative with respect to each other. A PESC and/or iPSC, which is 'differentiated' has a characteristic of a more specialized cell. Differentiated and undifferentiated cells are distinguished from each other by several well-established criteria, including morphological characteristics such as relative size and shape, ratio of nuclear volume to cytoplasmic volume; and expression characteristics such as detectable presence of known (gene) markers of differentiation.

In the present invention, the term 'maturation' as used herein refers to a biological process wherein a differentiated cell derived from PESC or iPSC exhibiting an immature state (or foetal state) of development is required to attain a more functional or a fully functional (including genetic and morphological) state of development under controlled conditions in in vitro culture. Therefore, maturation of PESC- and/or iPSC-derived foetal-like (immature) cardiomyocytes may be accompanied by the loss of foetal gene/protein expression, foetal morphological characteristics and associated functional characteristics, and the acquisition of gene expression, morphological characteristic and functional characteristics associated with adult (or adult-like) or mature cells. The process of "maturing" PESC- and/or iPSC-derived foetal-like (immature) cardiomyocytes leads to PESC- and/or iPSC-derived cardiomyocytes with a more adult-like or mature state of development.

The term 'cardiomyocytes' or 'cardiac myocytes' as used herein refers generally to any cardiomyocyte lineage cells, and can be taken to apply to cells at any stage of cardiomyocyte ontogeny, unless otherwise specified. For example, cardiomyocytes may include both cardiomyocyte precursor cells (immature cardiomyocytes or foetal cardiomyocytes) and mature cardiomyocytes (aduld-like cardiomyocytes). Further, cardiomyocytes can be subdivided into subtypes including, but not limited to, atrial cardiomyocyte, ventricular cardiomyocyte, sinoatrial node (SA) nodal cardiomyocyte, peripheral SA nodal cardiomyocyte, or central SA nodal cardiomyocyte.

The term 'foetal-like cardiomyocytes' or 'immature cardiomyocytes' as used herein refers to a cardiomyocyte derived from PESC and/or iPSC in in vitro culture, which does not possess the desired phenotype and/or genotype in relation to an adult or adult-like cardiomyocyte. For instance such foetal-like cardiomyocytes may exhibit automaticity (spontaneous contraction) and/or foetal-type ion channel expression, and/or foetal-type electrophysiological signals, and/or foetal-like gene expression patterns, and/or foetal-type physical phenotypes. Foetal-like (immature) cardiomyocytes can, for example, be distinguished from other cell types by using markers or lineage-specific markers including, but not limited to, MYH6, TNNT2, TNNI3, MLC2V, EMILIN2, SIRPA, VECAM, and others markers suitable for assessing a foetal or foetal-like stage of development (Burridge et al (2012) Stem Cell Cell, Vol. 10(1):16-28). The metabolic maturity can be determined by methods known to the skilled person, for examples methods that look at phenotype, morphology, gene expression, metabolic markers, cell surface markers, electrophysiological characteristics and/or cellular functional assay of the cell. For example, for maturation one can determine decreased expression of genes associated with a "foetal" state or cardiac hypertrophic state such as, for example, NPPA (BNA) and NPPB (BNP), or preferably, determine the electrophysiological characteristics of the maturing stem-cell derived cardiomyocytes, and wherein a more adult or adult-like cardiomyocyte characteristic can be seen for more maturated stem-cell derived cardiomyocytes, as discussed in detail herein.

In addition the relative maturity of stem-cell derived cardiomyocytes can be determined by the presence of decreased expression of genes associated with the a foetal state, such as NPPA, NPPB, smooth muscle actin and skeletal actin, or the increasing expression of adult genes/proteins, such as myosin light chain 2V, calsequestrin and ryanodine receptor).

The term 'adult-like cardiomyocytes' or 'mature cardiomyocytes' as used herein refers to cardiomyocytes which posses the desired phenotype and/or genotype in relation to an adult cardiomyocyte. In one embodiment, a mature cell has the phenotype and/or genotype of, but is not limited to, an adult cardiomyocyte or atrial cardiomyocyte or ventricular cardiomyocyte or SA nodal cardiomyocyte or peripheral SA nodal cardiomyocyte or central SA nodal cardiomyocyte. In other embodiments, adult-like cardiomyocytes' or 'mature cardiomyocytes' exhibit more mature electrophysiology patterns and/or more mature calcium handling patterns, and/or more adult-type ion channel expression, and/or more adult-type electrophysiological signals, and/or more adult-like contractile properties, and/or more adult-like gene expression patterns, and/or more adult-type physical (morphological) phenotypes when compared to foetal-like (immature) cardiomyocytes derived from PESC and/or iPSC in in vitro culture. Adult-like cardiomyocytes may also harbour greater degree of myofibril organization and sarcomeric striations, which are features that are poorly or insufficiently developed in the foetal-like (immature) cardiomyocytes derived from PESC and/or iPSC in in vitro culture.

The skilled person knows how to assess the maturity of PESC and/or iPSC-derived cardiomyocytes in in vitro culture, for example by using known cardiomyocyte-specific markers or lineage-specific markers relevant for a particular developmental stage as well as available methods in the art so as to distinguish adult-like (mature) cardiomyocytes from foetal-like (immature) cardiomyocytes. In the present invention, one way to assess maturity of a PESC and/or iPSC-derived cardiomyocyte in n vitro culture is to assess the expression of gene markers associated with the foetal (immature) state such as (but not limited to) NPPA, NPPB, smooth muscle actin, and skeletal actin. Decreased (gene) expression of one or more of said foetal (immature) markers would be indicative of an adult-like (mature) state. Another way to assess maturity of a PESC and/or iPSC-derived cardiomyocytes in in vitro culture is to assess the expression of gene markers associated with the adult-like (mature) state such as (but not limited to) myosin light chain 2V, casequestrin and ryanodine receptor. Increased (gene) expression of one or more of said adult-like (mature) markers would be indicative of an adult-like (mature) state (Burridge et al (2012), Stem Cell Cell, Vol. 10(1):16-28).

Another way to assess maturity of a PESC- and/or iPSC-derived cardiomyocytes in in vitro culture is to assess their electrophysiological properties, for instance the ability of a cell to generate and/or propagate an action potential in vitro. Electrophysiological maturity of a PESC and/or iPSC-derived cardiomyocytes in in vitro culture can be for instance assessed by patch clamp techniques, among other techniques. Changes that are indicative of an adult-like (mature) electrophysiological phenotype, in comparison to an foetal-like (immature) electrophysiological phenotype, include (but are not limited to) increased maximum upstroke velocity, decreased resting membrane potential, and increased amplitude of the action potential, which are hallmarks of an adult cardiomyocyte.

Another way to assess maturity of a PESC and/or iPSC-derived cardiomyocyte in in vitro culture is to assess their metabolic profile, for instance the mitochondrial activity in vitro culture. Maturity of the metabolic profile of a PESC and/or iPSC-derived cardiomyocyte in in vitro culture can be for instance assessed by using a TMRM assay (amongst other techniques), which utilizes the potentiometric red fluorescent dye tetramethylrhodamine methyl ester, commonly known as TMRM. Treatment with TMRM results in mitochondrial membrane potential-driven accumulation of TMRM within the inner membrane region of healthy functioning mitochondria. A non-limiting example of a characteristic change indicative of an adult-like (mature) metabolic profile, in comparison to a foetal-like (immature) metabolic profile, is the greater accumulation of TMRM in mitochondria of adult-like (mature) cardiomyocytes derived from foetal-like (immature) PESC and/or iPSC, which is detected by an increased TMRM-associated orange fluorescence in the TMRM assay.

Another way to assess maturity of a PESC and/or iPSC-derived cardiomyocyte in in vitro culture is to assess their morphological features, for instance the shape and/or ultra structural organization of the cytoskeleton. Maturity of the morphological features of a PESC and/or iPSC-derived cardiomyocyte in in vitro culture can be for instance assessed by immunohistochemistry techniques (amongst other techniques), for instance using immunofluorescence (Cy3 or Alexa-Fluor 647) and antibodies directed against integral constituents of the cytoskeleton, for instance alpha-actinin. Non-limiting examples of characteristic changes indicative of adult-like (mature) morphological features, in comparison to a foetal-like (immature) metabolic profile), is the greater polarization of cells, improved sarcomeric organization, and elongated shape.

In the present invention, the term 'markers' or 'lineage-specific markers' as used herein refers to a characteristic specifically associated with the phenotype of cells of a lineage of interest and can be used to assess the differentiation of an uncommitted cell to the lineage of interest. For instance, 'markers' or 'lineage-specific markers' can refer to nucleic acid or polypeptide molecules that are differentially expressed in a cell of interest. The detectable level of the marker nucleic acid or polypeptide is sufficiently higher or lower in the cells of interest compared to other cells, such that the cell of interest can be identified and distinguished from other cells using any of a variety of methods known in the art.

The term 'aqueous composition' as used herein refers to a composition that is water-based or to a composition in which the solvent is water. For instance, an aqueous composition can be obtained from dissolving (any) water-soluble substance(s) into water.

The term 'solid composition' as used herein refers to any composition that is in a solid form. The term 'solid composition' also encompasses compositions, which are in a semi-liquid form or semi-solid form. For instance, a solid composition may be in the form of a powder, granule, tablet, paste, puree, wet mixture, pellet, lyophilized form, freeze-dry form and the likes. In certain embodiments of the present invention, a solid composition can be dissolved in an appropriate amount solvent, for instance water, so as to obtain an aqueous composition as taught herein.

The term 'lipid' or 'lipids' as used herein refers to a group of molecules that include fats, waxes, sterols, fat-soluble vitamins (such as vitamins A, D, E, and K), monoglycerides, diglycerides, triglycerides, phospholipids, and others. Lipids can be divided into several categories including fatty acids, glycerolipids, glycerophospholipids, sphingolipids, saccharolipids, and polyketides (derived from condensation of ketoacyl subunits); and sterol lipids and prenol lipids (derived from condensation of isoprene subunits). The term 'lipids' also encompass molecules such as fatty acids and their derivatives (including tri-, di-, monoglycerides, and phospholipids), as well as other sterol-containing metabolites such as cholesterol. Further non-limiting examples of lipids include linolenic acid, linoleic acid and palmitic acid, arachidonic acid, DL-alpha-tocopherol acetate, ethyl alcohol, myristic acid, oleic acid, palmitoleic acid, PLURONIC® F-68 (polyoxyethylene-polyoxypropylene block copolymer), stearic acid, TWEEN® 80 (polysorbate 80), and others. The term 'lipid mixture' as used herein refers to the combination of at least two or more lipids.

The term 'serum-free culture medium' as used herein, is generally understood by the skilled person and refers to a medium substantially free of serum. By definition, serum-free medium lacks whole serum as an ingredient, but it may not be entirely free of serum-derived products, for example highly purified form of albumin, for example bovine or even human (recombinant) albumin may be included in such serum-free medium. For example, it may comprise up to 10 wt %, preferably up to 5 wt %, even more preferably up to 2 w %, up to 1 wt %, up to 0.5 wt %, or most preferably up to 0.25 wt % albumin, e.g. Bovostar BSA from Bovogen (Williams Ave Kellor East VIC 3033, Australia). Technical disadvantages to using serum include the undefined nature of serum, batch-to-batch variability in composition, and the risk of contamination. By the presence of such defined serum-derived products like the highly purified albumin, such disadvantages are not re-introduced in the serum-free medium.

The term 'mammal' as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and new born subjects, as well as foetuses, whether male or female, are intended to be included within the scope of this term.

The terms "a," "an" and "the" in their singular forms as used herein include plural referents unless the context dearly dictates otherwise. For example, a method for isolating "a" DNA molecule, includes isolating a plurality of molecules (e.g. 10's, 100's, 1000's, 10's of thousands, 100's of thousands, millions, or more molecules).

The term 'about', as used herein and unless specifically stated or obvious from context is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The term 'and/or' as used herein, refers to a situation wherein one or more of the stated cases may occur, alone or in combination with at least one of the stated cases, up to with all of the stated cases.

The term 'at least' as used herein refers to a situation wherein a particular value is the same as said particular value or more. For example, "at least 2" is understood to be the same as "2 or more" i.e., 2, 3, 4, 5, 6, 7, 8, 9, 10, 11, 12, 13, 14, 15, . . . , etc.

The terms "comprising" or "to comprise" and their conjugations, as used herein refer to a situation wherein said terms are used in their non-limiting sense to mean that items following the word are included, but items not specifically mentioned are not excluded. It also encompasses the more limiting verb "to consist of". In addition, reference to an element by the indefinite article "a" or "an" does not exclude the possibility that more than one of the elements is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

The term 'conventional techniques" as used herein refers to a situation wherein the methods of carrying out the conventional techniques used in methods of the invention will be evident to the skilled worker. The practice of conventional techniques in molecular biology, biochemistry, cell culture, genomics, sequencing and related fields are well-known to those of skill in the art and are discussed, for example, in the following literature references: Human Embryonic Stem Cell: The Practical Handbook. Publisher: John Wiley & Sons, LTD, Editors (Sullivan, S., Cowan, C. A., Eggan, K.) Harvard University, Cambridge, MA, USA (2007); Human Stem Cell, a Laboratory Guide ($2^{nd}$ Edition) by Peterson, S., and Loring, J. F. (2012).

The term "common scientific terms", unless defined otherwise, as used herein refers to technical and scientific terms used herein which have the same meaning as commonly understood by one of ordinary skill in the art to which this invention belongs. Singleton et al., Dictionary of Microbiology and Molecular Biology 2nd ed., J. Wiley & Sons (New York, N.Y. 1994); March, Advanced Organic Chemistry Reactions, Mechanisms and Structure 4th ed., J. Wiley & Sons (New York, N.Y. 1992); and Sambrook and Russel, Molecular Cloning: A Laboratory Manual 3rd ed., Cold Spring Harbor Laboratory Press (Cold Spring Harbor, N.Y. 2001) provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

The terms "less than" or "up to" and the like, as used herein refer the range from zero up to and including the value provided. For example, "less than 10" or "up to 10" is understood as 0, 1, 2, 3, 4, 5, 6, 7, 8, 9, or 10.

Throughout the present disclosure, when a mention is made for example of the term "2.5 microgram/ml of cholesterol", it is understood by the skilled person that "2.5 microgram/ml of cholesterol" is meant to denote 2.5 microgram of cholesterol per ml of culture medium.

As used herein, the term "three dimensional culture" is generally understood by the skilled person and refers to a method of culturing cells wherein cells are implanted or seeded into an artificial structure capable of supporting three-dimensional tissue formation. These structures, typically called scaffolds, are critical ex vivo as well as in vitro, to recapitulating the in vivo milieu and allowing cells to influence their own microenvironments.

As used herein, the term "isotonic solution", refers to a solution in which its effective osmole concentration is the same as the solute concentration of another solution or another cell and/or tissue with which it is compared. This occurs, for example, when the concentration of both water and total solute molecules are the same in an external solution as in the cell content. Water molecules diffuse through the plasma membrane in both directions, and as the rate of water diffusion is the same in both directions, that cell will neither gain nor lose water.

In the present invention, an isotonic composition refers to a solution wherein the concentration of both water and total solute molecules are the same in an external solution as in the cell content of the cell being preserved, transposed or stored in the composition of the present invention or as in the cell content of cells being part of a tissue and/or organ being preserved, transposed and/or stored in the composition of the present invention.

As used herein, the term "subject" refers to any vertebrate animal, but will typically pertain to a mammal, for example a human patient, a domesticated animal (such as dog or cat), a farm animal (such as horse, cow, or sheep) or a laboratory animal (such as rat, mouse, non-human primate or guinea pig). In preferred embodiments the subject is human, preferably an adult human.

Culture Medium Compositions of the invention

In a first aspect, the present invention relates to a water-based, aqueous culture medium composition. Particularly, the inventions relates to a culture medium composition, wherein said culture medium composition is essentially serum-free and comprises a thyroid hormone-like compound, a lipid mixture; and a carnitine compound.

In preparing the culture medium compositions of the present invention, it may be particularly advantageous to use a (chemically defined) serum-free medium to avoid serum lot-to-lot variation in their ability to support maturation and maintenance of foetal-like (immature) cardiomyocytes derived from PESC- and/or iPSC in in vitro culture. The use of a (chemically defined) serum-free culture medium is also advantageous to ensure reproducibility of results and maintain the yield and quality of adult-like (mature) cardiomyocytes cells obtained from maturating PESC- and/or iPSC-derived foetal-like (immature) cardiomyocytes in in vitro culture. The use of a (chemically defined) serum-free culture medium is also desirable to avoid the risk of potential pathogen contamination and to decrease immunogenicity of adult-like cardiomyocytes generated from PESC- and/or iPSC-derived foetal-like (immature) cardiomyocytes in in vitro culture. Chemically defined serum-free culture medium are well-known in the art and are commercially available. The skilled person in the art knows how to select an appropriate (chemically defined) serum-free culture medium for the preparation of the culture medium compositions of the invention. Non-limiting examples of commercially available and (chemically defined) serum-free culture media include, F-12 nutrient mixture (Ham), F-10 nutrient mixture, Leibovitz L-15, McCoy's 5A, MCDB 131, G-MEM, Improved MEM, DMEM, DMEM/F12, RPMI-1640, Waymouth's MB 752/1, Williams' Media E, IMDM, Media 199, Opt-MEM, Modified Eagle, Medium (MEM), Minimal Essential Medium (MEM), BGJb (Fitton-Jackson Modification), CMRL, BME. Mixture of one or more chemically specified serum-free media can be employed in the culture medium compositions of the present invention. A non-limiting example of a mixture of two chemically specified serum-free culture media is for instance a mixture comprising IMDM and F12 nutrient (Ham). Said mixture was shown to be particularly suitable for the preparation of the culture medium compositions of the present invention.

The present inventor found that the addition of thyroid hormone-like compound in the culture medium compositions of the invention greatly promotes and improves maturation of cardiomyocytes obtained from PESC-derived foetal-like (immature) cardiomyocytes and/or iPSC-derived foetal-like (immature) cardiomyocytes in in vitro culture. Specifically, it was found that exposing foetal-like (immature) cardiomyocytes derived from PESC and/or iPSC in in vitro culture to at least one thyroid-like hormone compound resulted in enhanced maturation of electrophysiological and mechanical attributes (e.g. adult-like action potential, lower resting membrane potential and stronger rhythmic contractions of cardiac muscle cells). Enhanced maturation of calcium homeostasis (i.e. calcium currents), enhanced maturation of the ultrastructural organization of cardiomyocytes (i.e. appearance of an organized striated pattern and elongated shape resembling the adult phenotype), and enhanced maturation of other characteristics proper to an adult or adult-like (mature) cardiomyocyte phenotype such as metabolic profile (e.g. enhanced mitochondrial activity), and detection of adult stage-specific gene markers such as troponin I and alpha actinin and the likes) may also be detected.

The present inventor also surprisingly found that adding at least one thyroid hormone-like compound in the culture medium compositions of the invention enhanced survival of adult-like (mature) cardiomyocytes generated from PESC-derived foetal-like (immature cardiomyocytes and/or iPSC-derived foetal-like (immature) cardiomyocytes in in vitro culture compared to a situation where no thyroid hormone-like compound is present in the culture medium compositions of the invention. It was observed that this effect also globally increased the yield of adult-like cardiomyocytes generated from PESC-derived foetal-like (immature cardiomyocytes and/or iPSC-derived foetal-like (immature) cardiomyocytes in in vitro culture, obtainable by the method of the present invention.

Suitable thyroid hormone-like compounds for the preparation of the culture medium of the present invention include, but is not limited to, T3, T4 (which is a thyroid hormone than can be converted into T3 by 5'-iodinase, see below), DITPA, and thyroid hormone agonist compounds such as for example GC-1 compound, RO compound, CO23 compound, KB2115 compound, and the like. T3 is a naturally occurring tyrosine-based hormone produced by the thyroid gland, which is produced during ontogenesis. Another form of thyroid hormone in the blood is thyroxine (T4), which has a longer half-life than T3. The ratio of T4 to T3 released into the blood is roughly 20 to 1. T4 is converted to the active T3 (three to four times more potent than T4) within cells by deiodinases (5'-iodinase). T3 and T4 are well known in the art and are commercially available.

In an embodiment, the thyroid-like hormone compound is triiodothyronine (T3) and/or 3,5-diiodothyropropionic acid (DITPA).

In one embodiment, the culture medium composition of the invention comprises about 1.0 to about 150 ng/ml of thyroid hormone-like compound, preferably about 10 to about 125 ng/ml of thyroid hormone-like compound, preferably about 25 to about 100 ng/ml of thyroid hormone-like compound, preferably about 30 to about 75 ng/ml of thyroid hormone-like compound, preferably about 40 to about 60 ng/ml of thyroid hormone-like compound, preferably about 53 to about 55 ng/ml of thyroid hormone-like compound.

For instance, non-limiting examples of concentration for the thyroid hormone-like compound that may be used in the culture medium composition as taught herein and/or in the method as taught herein and/or in the kit as taught herein may include about 0.0001 to about 500 ng/ml of thyroid hormone-like compound, preferably about 0.001 to about 400 ng/ml of thyroid hormone-like compound, preferably about 0.05 to about 300 ng/ml of thyroid hormone-like compound, preferably about 0.075 to about 200 ng/ml of thyroid hormone-like compound, more preferably about 0.09 to about 110 ng/ml of thyroid hormone-like compound.

In an embodiment, the culture medium composition of the invention comprises about 25 to about 150 ng/ml of thyroid hormone-like compound.

In a preferred embodiment, the culture medium composition of the invention comprises about 50 ng/ml of thyroid hormone-like compound, for example 40 to 60 ng/ml of thyroid hormone-like compound. //pct In one embodiment, the culture medium composition of the invention comprises about 1.0 to about 150 ng/ml of T3, preferably about 10 to about 125 ng/ml of T3, preferably about 25 to about 100 ng/ml of T3, preferably about 30 to about 75 ng/ml of T3, preferably about 40 to about 60 ng/ml of T3, preferably about 53 to about 55 ng/ml of T3.

For instance, non-limiting examples of concentration for the thyroid hormone-like compound that may be used in the culture medium composition as taught herein and/or in the method as taught herein and/or in the kit as taught herein may include about 0.0001 to about 500 ng/ml of T3, preferably about 0.001 to about 400 ng/ml of T3, preferably about 0.05 to about 300 ng/ml of T3, preferably about 0.075 to about 200 ng/ml of T3, more preferably about 0.09 to about 110 ng/ml of T3.

In an embodiment, the culture medium composition of the invention comprises about 25 to about 150 ng/ml of T3.

In a preferred embodiment, the culture medium composition of the invention comprises about 50 ng/ml of T3, for example 40 to 60 ng/ml of T3.

In an embodiment, the culture medium composition of the invention comprises about 25 ng/ml to about 150 ng/ml of T3 and/or about 1 microM to about 2 microM of DITPA.

In an embodiment, the culture medium composition of the present invention comprises at least one thyroid hormone-like compound selected from the group consisting of T3 and DITPA.

In an embodiment of the invention, T3 and DITPA can be used interchangeably or in combination in the culture medium compositions and/or the method of the invention. In preferred embodiment, T3 is used in the culture medium compositions and/or the methods of the invention.

In another embodiment, T3 and/or DITPA can be used in combination with one or more thyroid hormone-like compounds selected from T4, thyroid hormone agonist compounds such as for example GC-1 compound, RO compound, CO23 compound, KB2115 compound, and the like.

In another embodiment, the culture medium composition of the invention comprises about 0.01 nM to 10 microM of DITPA, preferably about 0.1 nM to 8 microM of DITPA, preferably about 0.2 nM to 6 microM of DITPA, preferably 0.3 nM to 5 microM of DITPA, preferably about 0.4 nM to 4 microM of DITPA, preferably about 0.5 nM to 3 microM of DITPA, preferably about 0.6 nM to 2 microM of DITPA, more preferably about 0.75 nM to 1.5 microM of DITPA.

In an embodiment, the culture medium composition of the invention comprises at least about 1 nM of DITPA, preferably about 1 microM of DITPA, but preferably no more than about 10 microM of DITPA.

In a preferred embodiment, the composition of the invention comprises about 0.1 to 100 ng/ml of T3 and about 1 nM to 1 microM of DITPA.

In an embodiment, the culture medium compositions as taught herein may comprise both T3 and DITPA. Suitable amounts or concentration of T3 and DITPA can be determined by the skilled person, based on the information disclosed herein. For example, suitable concentrations for T3 and DITPA may be at least about 0.1 ng/ml of T3 and at least about 1 nM of DITPA, more preferably about 100 ng/ml of T3 and about 1 microM of DITPA. Another example of suitable concentrations may be at least about 25 ng/ml of T3 and at least about 1 nM of DITPA, more preferably about 50 ng/ml of T3 and about 1 microM of DITPA.

Other thyroid hormone-like compounds, thyroid hormone derivatives, and precursors of thyroid hormone can also be used to prepare the culture medium composition according to the invention as taught herein but T3 and/or DITPA are preferable. The skilled person also knows how to select suitable and effective thyroid hormone-like compounds, thyroid hormone derivatives, and precursors of thyroid hormone, and knows how to determine effective dosages based on the information disclosed herein.

In one embodiment, the lipid mixture comprises cholesterol and one or more lipid selected from linolenic acid, linoleic acid, and palmitic acid.

The present inventor has found that the addition of a lipid mixture to the culture media composition as taught herein is beneficial for culturing and maturing foetal-like cardiomyocytes, derived from PESC and/or iPSC in in vitro culture, into adult-like (mature) and maintaining said adult-like cardiomyocytes for a prolonged period of time in an in vitro culture milieu. Without being bound to any theories, the addition of a (chemically defined) lipid mixture in the culture medium composition of the invention is believed to render said culture medium more concordant with the natural in vivo environment in which PESC-derived foetal-like (immature) cardiomyocytes and/or iPSC-derived foetal-like (immature) cardiomyocytes mature into adult-like (mature) cardiomyocytes. The present inventor has found that the presence of a chemically defined lipid mixture in the culture media composition of the invention optimizes maturation and survival of PESC-derived foetal-like (immature) cardiomyocytes and/or iPSC-derived foetal-like (immature) cardiomyocytes in in vitro culture. Presence of a chemically defined lipid mixture in the culture medium compositions of the present invention appears particularly advantageous to support and accommodate the changes in energy metabolism (i.e. mitochondrial metabolism) that occur in maturing cardiomyocytes generated from PESC-derived foetal (immature) cardiomyocytes and/or iPSC-derived foetal-like (immature) cardiomyocytes in in vitro culture.

In a preferred embodiment, the lipid mixture comprises cholesterol, linolenic acid, linoleic acid, and palmitic acid. Cholesterol, linolenic acid, and linoleic acid are well known in the art and commercially available.

In an embodiment, the culture medium of the composition of the invention comprises about 1 microgram/ml to about 4 microgram/ml of cholesterol.

In an embodiment, the culture medium of the composition of the invention comprises about 0.01 to 5 microgram/ml of cholesterol, preferably about 0.1 to 4.5 microgram/ml of cholesterol, preferably about 1.0 to 4.0 microgram/ml of cholesterol, preferably about 1.5 to 3.0 microgram/ml of cholesterol more preferably about 2.0 to 2.5 microgram/ml of cholesterol.

In an embodiment of the invention, the culture medium composition comprises about 0.01 to about 20 microgram/ml of linolenic acid, preferably about 0.04 to about 18 microgram/ml of linolenic acid, preferably about 0.06 to about 16 microgram/ml of linolenic acid, preferably about 0.08 to about 14 microgram/ml of linolenic acid, preferably about 0.09 to about 12 microgram/ml of linolenic acid, preferably about 0.095 to about 11 microgram/ml of linolenic acid, more preferably about 0.1 to about 10 microgram/ml of linolenic acid.

For Instance, non-limiting examples of concentration for the linolenic acid that may be used in the culture medium composition as taught herein and/or in the method as taught herein and/or in the kit as taught herein may include about 0.001 to 0.5 microgram/ml of linolenic acid, preferably about 0.005 to 0.4 microgram/ml of linolenic acid, preferably about 0.0075 to 0.3 microgram/ml of linolenic acid, preferably about 0.01 to 0.2 microgram/ml of linolenic acid, more preferably about 0.075 to 0.15 microgram/ml of linolenic acid.

In a preferred embodiment, the culture medium composition comprises about 0.1 microgram/ml of linolenic acid, for example 0.05 to 0.3 microgram/ml of linolenic acid.

In an embodiment of the invention, the culture medium composition comprises about 0.01 to about 20 microgram/ml of linoleic acid, preferably about 0.04 to about 18 microgram/ml of linoleic acid, preferably about 0.06 to about 16 microgram/ml of linoleic acid, preferably about 0.08 to about 14 microgram/ml of linoleic acid, preferably about 0.09 to about 12 microgram/ml of linoleic acid, preferably about 0.095 to about 11 microgram/ml of linoleic acid, more preferably about 0.1 to about 10 microgram/ml of linoleic acid.

For instance, non-limiting examples of concentration for the linoleic acid that may be used in the culture medium composition as taught herein and/or in the method as taught herein and/or in the kit as taught herein may include about 0.001 to 0.5 microgram/ml of linoleic acid, preferably about 0.005 to 0.4 microgram/ml of linoleic acid, preferably about 0.0075 to 0.3 microgram/ml of linoleic acid, preferably about 0.01 to 0.2 microgram/ml of linoleic acid, more preferably about 0.075 to 0.15 microgram/ml of linoleic acid.

In a preferred embodiment, the culture medium composition comprises about 0.1 microgram/ml of linoleic acid, for example 0.05 to 0.3 microgram/ml of linoleic acid.

In an embodiment of the invention, the culture medium composition comprises about 0.01 to about 20 microgram/ml of palmitic acid, preferably about 0.04 to about 18 microgram/ml of palmitic acid, preferably about 0.06 to about 16 microgram/ml of palmitic acid, preferably about 0.08 to about 14 microgram/ml of palmitic acid, preferably about 0.09 to about 12 microgram/ml of palmitic acid, preferably about 0.095 to about 11 microgram/ml of palmitic acid, more preferably about 0.1 to about 10 microgram/ml of palmitic acid.

For instance, non-limiting examples of concentration for the palmitic acid that may be used in the culture medium composition as taught herein and/or in the method as taught herein and/or in the kit as taught herein may include about 0.001 to 0.5 microgram/ml of palmitic acid, preferably about 0.005 to 0.4 microgram/ml of palmitic acid, preferably about 0.0075 to 0.3 microgram/ml of palmitic acid, preferably about 0.01 to 0.2 microgram/ml of palmitic acid, more preferably about 0.075 to 0.15 microgram/ml of palmitic acid.

In a preferred embodiment, the culture medium composition comprises about 0.1 microgram/ml of palmitic acid, for example 0.05 to 0.3 microgram/ml of palmitic acid.

In an embodiment, the inventor found that a culture medium composition of the present invention is particularly effective in maturing foetal-like (immature) cardiomyocytes derived from PESC and/or iPSC into adult-like (mature) cardiomyocytes in in vitro culture when said culture medium composition comprises about 2.2 microgram/ml of cholesterol, about 0.1 microgram/ml of linolenic acid, about 0.1 microgram/ml of linoleic acid, and about 0.1 microgram/ ml of palmitic acid, compared to a situation where the culture medium compositions of the invention lacks this particular lipid mixture.

In an embodiment, it may be advantageous, although not essential, to enlarge the lipid mixture by adding other lipids to the culture medium compositions of the invention.

In one embodiment, the lipid mixture may further comprises one or more components selected from the group of arachidonic acid, DL-alpha-tocopherol acetate, ethyl alcohol, myristic acid, oleic acid, palmitoleic acid, PLURONIC® F-68 (polyoxyethylene-polyoxypropylene block copolymer), stearic acid, TWEEN 80 (polysorbate 80).

In an embodiment, the lipid mixture may further comprises two or more lipids selected from arachidonic acid, DL-alpha-tocopherol acetate, ethyl alcohol, myristic acid, oleic acid, palmitoleic acid, PLURONIC® F-68 (polyoxyethylene-polyoxypropylene block copolymer), stearic acid, TWEEN® 80 (polysorbate 80). The present inventor has found that the addition, in the culture medium compositions as taught herein, of two or more lipids selected from arachidonic acid, DL-alpha-tocopherol acetate, ethyl alcohol, myristic acid, oleic acid, palmitoleic acid, PLURONIC® F-68 (polyoxyethylene-polyoxypropylene block copolymer), stearic acid, TWEEN® 80 (polysorbate 80), resulted in a culture medium composition that was more efficient in terms of its ability to promote and enhance maturation of foetal-like (immature) cardiomyocytes derived from PESC and/or iPSC in in vitro culture compared to a situation where the culture medium composition as taught herein does not contain this particular lipid mixture.

In a preferred embodiment, the lipid mixture comprises cholesterol, linoleic acid, linolenic acid, palmitic acid, arachidonic acid, DL-alpha-tocopherol acetate, ethyl alcohol, myristic acid, oleic acid, palmitoleic acid, PLURONIC® F-68 (polyoxyethylene-polyoxypropylene block copolymer), stearic acid, TWEEN® 80 (polysorbate 80).

The present inventor found that adding, in the culture medium compositions as taught herein, a lipid mixture comprising cholesterol, linoleic acid, linolenic acid, palmitic acid, arachidonic acid, DL-alpha-tocopherol acetate, ethyl alcohol, myristic acid, oleic acid, palmitoleic acid, PLURONIC® F-68 (polyoxyethylene-polyoxypropylene block copolymer), stearic acid, TWEEN® 80 (polysorbate 80), resulted in an even greater effects on the maturation of foetal-like (immature) cardiomyocytes derived from PESC and/or iPSC in in vitro culture, so as to obtain adult-like (mature) cardiomyocytes, compared to a situation where the culture medium compositions of the invention lacks this particular lipid mixture.

The skilled person knows how to prepare an appropriate lipid mixture using the information disclosed herein. Chemically defined lipid mixture comprising cholesterol, linoleic acid, linolenic acid, palmitic acid, arachidonic acid, DL-alpha-tocopherol acetate, ethyl alcohol, myristic acid, oleic acid, palmitoleic acid, PLURONIC® F-68 (polyoxyethylene-polyoxypropylene block copolymer), stearic acid, TWEEN® 80 (polysorbate 80) are known in the art and can be purchased from commercial suppliers. A non-limiting example of a commercially available lipid mixture, which is suitable for the present invention is Gibco's Chemically Defined lipid Concentrate (catalogue #11905-031, quantity: 100 mL), which is characterised in that it contains 2.0 mg/L of arachidonic acid, 220 mg/L of cholesterol, 70 mg/L of DL-alpha-tocopherol acetate, confidential levels of ethyl alcohol 100%, 10 mg/L of linoleic acid, 10 mg/L of linolenic acid, 10 mg/L of myristic acid, 10 mg/L of oleic acid, 10 mg/L of palmitic acid, 10 mg/L of palmitoleic acid, 90000 mg/L of PLURONIC® F-68 (polyoxyethylene-polyoxypropylene block copolymer), stearic acid, 10 mg/L of stearic acid, 2200 mg/L of TWEEN® 80 (polysorbate 80). Furthermore, other lipid mixtures comprising a different composition of lipids and derivatives thereof, resent at similar or different concentrations, may also be used in the culture medium of the present invention but it would be preferable to use the lipid mixtures as taught herein. The skilled person knows how to prepare alternative lipid mixtures, knows how to select individual lipids and derivatives thereof, and knows how to select the appropriate effective dosages, so that the efficiency as disclosed herein of the culture medium according to the present invention is preserved.

In preparing the culture medium compositions as taught herein, it might be particularly advantageous to add carnitine to the culture medium composition. Without being bound to any theory, the present inventor found that carnitine is advantageous for promoting bioenergetics pathways (e.g. mitochondrial activity) during differentiation and maturation of foetal-like (immature) cardiomyocytes derived from iPSC and/or iPSC in in vitro culture.

In one embodiment, the culture medium composition of the invention may comprise about 0.5 mM to about 3.5 mM of carnitine.

In another embodiment, the culture composition of the invention may comprise about 0.01 to 5 mM of carnitine, preferably about 0.1 to 4 mM of carnitine, preferably about 0.5 to 3 mM of carnitine, preferably about 1.0 to 2.5 mM of carnitine, more preferably about 1.5 to 2.25 mM of carnitine.

In one embodiment, the culture medium composition as taught herein may further comprise a creatine compound and a taurine compound.

Without being bound to any theories, the present inventor found that it may be advantageous to add creatine to the culture medium compositions of the invention so as to prevent or alleviate cell death, and taurine so as to prevent or alleviate ischemia-induced cell necrosis and apoptosis in in vitro culture. The present inventor also observed that the presence of T3, carnitine, creatine and taurine in the culture medium composition of the invention represents a powerful combination in the sense that the presence of said combination in the culture medium compositions as taught herein enhances maturation of foetal-like (immature) cardiomyocytes derived from PESC and/or iPSC in in vitro culture while promoting at the same time their survival inn vitro culture. This effect is also associated with an increase in the yield (greater number) of adult-like (mature) cardiomyocytes obtained from foetal-like (immature) cardiomyocytes derived from PESC and/or iPSC in in vitro culture by the methods as taught herein.

In one embodiment, the culture medium composition of the invention may comprise about 3.0 mM to about 7.0 mM of creatine.

In an embodiment, the culture medium composition of the invention may comprise about 2.0 mM to about 7.0 mM of taurine.

In an embodiment, the culture medium composition of the invention may comprise about about 1 to 10 mM of creatine, preferably about 2 to 8 mM of creatine, preferably about 3 to 7 mM of creatine, preferably about 3.5 to 6.0 mM of creatine, more preferably about 4.5 to 5.5 mM of creatine.

In an embodiment, the culture medium composition of the invention may comprise about 1.0 to about 25 mM of taurine, preferably about 2.0 to about 20 mM of taurine, preferably about 3 to about 15 mM of taurine, preferably about 4.0 to about 10 mM of taurine, preferably about 4.5 to about 7 mM of taurine, more preferably about 5 mM of taurine.

For instance, non-limiting examples of concentration for taurine that may be used in the culture medium composition as taught herein and/or in the method as taught herein and/or in the kit as taught herein may include about 0.01 to about 5 mM of taurine, preferably about 0.1 to about 4 mM of taurine, preferably about 0.5 to about 3 mM of taurine, preferably about 1.0 to about 2.5 mM of taurine, more preferably about 1.5 to about 2.25 mM of taurine.

In a preferred embodiment, the culture medium composition of the invention may comprise about 0.01 to 5 mM of carnitine, preferably about 0.1 to 4 mM of carnitine, preferably about 0.5 to 3 mM of carnitine, preferably about 1.0 to 2.5 mM of carnitine, more preferably about 1.5 to 2.25 mM of carnitine, and about 1 to 10 mM of creatine, preferably about 2 to 8 mM of creatine, preferably about 3 to 7 mM of creatine, preferably about 3.5 to 6.0 mM of creatine, more preferably about 4.5 to 5.5 mM of creatine, and about 1.0 to 25 mM of taurine, preferably about 2.0 to 20 mM of taurine, preferably about 3 to 15 mM of taurine, preferably about 4.0 to 10 mM of taurine, preferably about 4.5 to 7 mM of taurine, more preferably about 5 mM of taurine.

In a preferred embodiment of the invention, it was found that optimal results were obtained when the culture medium compositions as taught herein comprised about 2 mM of carnitine, about 5 mM of creatine, and about 5 mM of taurine was also observed that the L-carnitine was particularly suitable for the preparation of the culture medium composition as taught herein.

In an embodiment, the culture medium of the invention may further comprise about 1 mg/L to about 50 mg/L of insulin, preferably about 3 mg/L to about 40 mg/L of insulin, preferably about 5 mg/L to about 30 mg/L of insulin, preferably about 7 mg/L to about 20 mg/L of insulin, preferably about 9 mg/L to about 12 mg/L of insulin, preferably about 9.5 mg/L to about 10.5 mg/L of insulin, more preferably about 10 mg/L of insulin.

In another embodiment, the culture medium of the invention may further comprises about 1 mg/L to about 25 mg/L of transferrin, preferably about 1.5 mg/L to about 20 mg/L of transferrin, preferably about 2 mg/L to about 15 mg/L of transferrin, preferably about 2.5 mg/L to about 10 mg/L of transferrin, preferably about 3 mg/L to about 8 mg/L of transferrin, preferably about 3.5 mg/L to about 7 mg/L of transferrin, preferably about 4 mg/L to about 6 mg/L of transferrin, preferably about 4.5 mg/L to about 5.7 mg/L of transferrin, more preferably 5.5 mg/L of transferrin.

In further embodiment, the culture medium of the invention may further comprise about 0.001 mg/L to about 0.01 mg/L of selenium (or sodium selenite), preferably about 0.002 mg/L to about 0.009 mg/L of selenium (or sodium selenite), preferably about 0.003 mg/L to about 0.008 mg/L of selenium (or sodium selenite), preferably about 0.004 mg/L to about 0.0075 mg/L of selenium (or sodium selenite), preferably about 0.005 mg/L to about 0.007 mg/L of selenium (or sodium selenite), preferably about 0.006 mg/L to about 0.0069 mg/L of selenium (or sodium selenite), preferably about 0.0065 mg/L to about 0.0068 mg/L of selenium (or sodium selenite), more preferably about 0.0067 mg/L of selenium (or sodium selenite).

In a preferred embodiment, the culture medium of the invention may further comprise about 5 mg/L to about 15 mg/L of insulin, and about 3 mg/L to about 8 mg/L of transferrin, and about 0.005 mg/L to about 0.0075 mg/L of selenium (or sodium selenite).

In a preferred embodiment, the culture medium compositions as taught herein may comprise about 10 mg/L of insulin, about 5.5 mg/L of transferrin and about 0.0067 mg/L of selenium (or sodium selenite).

Insulin, transferring and selenium are well-known in the art and are commercially available. A non-limiting example of commercially available preparation comprising insulin, transferrin and selenium is Gibco's insulin-Transferrin-Selenium Ethanolamine Solution (ITS-X) preparation (catalogue #51500, quantity: 10 mL), which is characterised in that it contains 1000 mg/L (0.17 mM) of insulin, 550 mg/L (6.87 mM) of transferrin, 0.67 mg/L (0.0038 mM) of sodium selenite, 200 mg/ml (3.27 mM) of ethanolamine.

In an embodiment, the culture medium compositions as taught herein may further comprise one or more trace elements. It was found by the present inventor that the presence of one or more trace elements in the culture medium is particularly advantageous for promoting maturation of foetal-like (immature) cardiomyocytes derived from PESC and/or iPSC in in vitro culture compared to a situation where the culture medium compositions as taught herein lack one or more trace elements. The presence of one or more trace elements was also found to be advantageous for maintaining adult-like (mature) cardiomyocytes generated from PESC-derived foetal-like (immature) cardiomyocytes and/or iPSC-derived foetal-like (immature) cardiomyocytes in in vitro culture for a prolonged period of time, for instance up to several months compared to a situation where the culture medium compositions as taught herein lack one or more trace elements. It was also found by the inventor that the addition of one or more trace elements was beneficial to increase the yield (quantity) and quality of adult-like (mature) cardiomyocytes obtained from PESC-derived foetal-like (immature) cardiomyocytes and/or iPSC-derived foetal-like (immature) cardiomyocytes in in vitro culture compared to a situation where the culture medium compositions as taught herein lack one or more trace elements. Without being bound to any theories, the presence of one or more trace elements provides anti-oxidant activity among other beneficial biological actions. The one or more trace elements is/are preferably present as ions or chelated complexes. The ions may be simple ions comprising only a single element or may be complex ions comprising two or more elements. The ions may be simple ions comprising only a single element or may be complex ions comprising two or more elements. Preferably the elements may be transition metal elements, e.g., elements selected from the group consisting of Sc, TI, V, Cr, Mn, Fe, Co, Ni, $Cu_5$ Zn, Ga, As, Se, Br, Ai, Si, P, Y, Zr, Nb, Mo, Tc, Ru, Rh, Rb, Ce, Ag, Pd, Ag, Cd, In, Sn, Sb, F, Te, Au, $Pt_5$ Bi, Ir, Os, Re, W, Ta and Hf.

In one embodiment, the culture medium composition of the invention may comprise one or more trace elements, preferably all, selected from the group of Mn, Si, Mb, V, Ni, Sn, AL, Ag, Ba, K, Cd, Co, CR, F, Ge, I, Rb, and Zr.

In another embodiment, the one or more trace elements may be selected from $MnSO_4·H_2O$, $Na_2SiO_3·9H_2O$, molybdic acid ammonium salt $((NH_4)_6Mo_7O_{24}·4H_2O)$, $NH_4VO_3$, $NISO_4·6H_2O$, $SnCl_2$ (anhydrous), $AlCl_3·6H_2O$, $AgNO_3$, $Ba(C_2H_3O_2)_2$, KBr, $CdCl_2$, $CoCl_2·6H_2O$, $CrCl_3$ (anhydrous), NaF, $GeO_2$, KI, RbCl, and $ZrOCl_2·8H_2O$.

In preferred embodiment, the culture medium composition of the invention may comprise $MnSO_4·H_2O$, $Na_2SiO_3·9H_2O$, molybdic acid ammonium salt $((NH_4)_6Mo_7O_{24}·4H_2O)$, $NH_4VO_3$, $NISO_4·6H_2O$, $SnCl_2$ (anhydrous), AlCl3.6H2O, AgNO3, Ba(C2H3O2)2, KBr, CdCl2, CoCl2.6H2O, CrCl3 (anhydrous), NaF, GeO2, KI, RbCl, and ZrOCl2.8H2O.

Trace element formulations suitable for the preparation of the culture medium as though therein are known in the art and are commercially available. For instance, commercially available trace element formulation B (cat. No 25-02 from Corning) and trace element formulation C (cat. No 25-023 from Corning) can be used in the present invention. The present inventor found that for optimal results, it is preferably to mix formulation C with formulation B in a ratio of about between 30:1 and 1 30, preferably 5:1-20:1. More preferably 10:1 (i.e. 10 times more formulation C over formulation B). The skilled person knows how to prepare trace element mixture and how to select an effective ratio. For instance, a trace element mixture resulting from mixing formulation C with formulation B in a ratio of 10:1 (i.e. 10 times more formulation C over formulation B) can be obtained by adding about 0.05 ml to 5 ml of formulation B into 10 000 ml of culture medium, preferably about 0.01 to 4 ml of formulation B into 10 000 ml of culture medium, preferably about 0.5 ml to 3 ml of formulation B into 10 000 ml of culture medium, preferably 0.75 ml to 2 ml of formulation B into 10 000 ml of culture medium, more preferably about 1 ml of formulation B into 10 000 ml of culture medium, as well as by adding about 0.05 ml to 5 ml of formulation C into 1000 ml of culture medium, preferably about 0.01 to 4 ml of formulation C into 1000 ml of culture medium, preferably about 0.5 ml to 3 ml of formulation C into 1000 ml of culture medium, preferably 0.75 ml to 2 ml of formulation C into 1000 ml of culture medium, more preferably about 1 ml of formulation C into 1000 ml of culture medium, in a ratio as, for example given above, e.g. a ratio of C to B of 10:1. Other equivalent trace element mixtures resulting from mixing other trace element formulations or resulting from the use of homemade formulations or mixtures can also be used for the preparation of the culture medium composition according to the present invention but the trace element(s) and trace element mixture(s) as taught herein are preferred.

In one embodiment, the culture medium compositions as taught herein may further comprise polyvinyl alcohol (PVA). Without being bound to any theories, the present inventor has found that the presence of PVA in the culture medium composition of the invention Is particularly advantageous to promote the formation and maintenance of a three-dimensional arrangement between foetal-like (immature) cardiomyocytes derived from PESC and/or iPSC in in vitro culture compared to a situation where the culture medium compositions as taught herein lack PVA. The same advantages were also observed for adult-like (mature) cardiomyocytes generated from foetal-like (immature) cardiomyocytes derived from PESC and/or iPSC in in vitro culture.

PVA is well known in the art and can be commercially purchased. PVA analogues or derivatives can also be used for the preparation of the culture medium according to the present invention but PVA as disclosed herein is preferred. The skilled person knows how to prepare and dissolve PVA to obtain a suitable PVA liquid form.

In an embodiment, the culture medium of the invention may further comprise 2 mg/ml to about 7 mg/ml of PVA.

In an embodiment of the invention, the culture medium composition may comprise about 0.1 to 10 mg/ml of PVA, preferably about 3 to 8 mg/ml of PVA, more preferably about 4 to 6 mg/ml of PVA.

In a preferred embodiment, the culture medium composition may comprise at least about 1.25 mg/ml of PVA, preferably about 5 mg/ml of PVA.

In an embodiment, the culture medium of the invention may further comprise comprises one or more compounds selected from the group of essential and non-essential amino acids, vitamins, organic constituents, inorganic salts, highly purified bovine serum albumin, growth supplement (e.g. Ham's F12 nutrient mix), antioxidants, antibiotics, monothiolglycerol, glutamine and glucose. The culture medium composition may also further comprise a physiologically acceptable saline solution, preferably an isotonic saline solution.

In a preferred embodiment, the culture medium composition of the invention may further comprise bovine serum albumin, glucose, vitamins, antibiotics, monothiolglycerol, glutamine, amino acids, and Ham's F12 nutrient mix.

The present inventor has found that it may be advantageous to use a serum-free culture medium that has a lower glucose content relative to standard serum-free culture media, for the preparation of the culture medium of the invention. For instance, standard serum-free media contain about 3000 mg/L of glucose (17.5 mM). Commercially available low-glucose serum-free culture medium contain about 1000 mg/L of glucose (5.5 mM).

In an embodiment, such low-glucose serum-free culture medium formulation may be used for the preparation of the culture medium composition of the invention. A dilution of a commercially available low-glucose serum-free culture medium or any other homemade formulations can be used in the preparation of the culture medium composition according to the present invention.

In an embodiment, the culture medium compositions as taught herein may comprise about 1 to 10 mM of glucose, preferably about 2 to 8 mM of glucose, preferably 3 to 7 mM of glucose, preferably 4.5 to 6.5 mM of glucose, more preferably about 5.0 to 6.0 mM of glucose.

In a preferred embodiment, the culture medium composition as taught herein may comprise at least about 1 mM of glucose and no more than about 5.5 mM of glucose.

In a further embodiment, the culture medium composition as taught herein may comprise about 10 to 200 microM of glucose, preferably about 25 to 150 microM of glucose, more preferably about 45 to 120 microM of glucose. Preferably, the culture medium composition may comprise at least about 55 microM of glucose and no more than about 111 microM of glucose.

In an embodiment, the culture medium composition of the invention may be glucose-free. In yet another embodiment, the glucose is D-glucose.

In one embodiment, the culture medium composition as taught herein may be in a liquid form, a semi-liquid form or a solid form or semi-solid form. In a preferred embodiment, the culture medium composition of the invention is in a liquid form.

In one embodiment, the culture medium composition as taught herein may be a solid composition, preferably a powder composition, wherein the composition can be dissolved in an aqueous solution so as to obtain the compositions as taught herein.

Non-limiting examples of solid forms include powder, granule, crystal, tablet, paste, puree, wet mixture, pellet, lyophilized form, freeze-dry form and the likes.

In a preferred embodiment, the solid form is a powder.

The culture medium compositions as taught herein may also be referred to as a 'maturation medium compositions'.

The culture medium composition as taught herein may lack a thyroid hormone-like compound. In other words, the same medium, having the identical composition(s) as detailed above, but without the addition or presence of any thyroid hormone-like compound, may be used in maturing foetal-like (immature) cardiomyocytes derived from PESC and/or iPSC in in vitro culture using the methods or kits as disclosed herein.

The present inventor found that this alternative culture composition medium of the invention (i.e. without the thyroid hormone-like compound) may be used to mature foetal-like (immature) cardiomyocytes derived from PESC and/or iPSC in in vitro culture, as can be witnessed from the examples. However, the present inventor observed that the effects of the culture medium composition as taught herein, but lacking a thyroid hormone-like compound, on the maturation of foetal-like cardiomyocytes derived from PESC and/or iPSC in in vitro culture, are less pronounced (less efficient, less robust) that what is achievable (as taught herein) with the culture medium composition of the invention, but which comprises at least one thyroid hormone-like compound. This alternative medium, i.e. having the identical compositions as detailed above, but without the presence of any thyroid hormone-like compound may be used alone, or in combination with the medium disclosed herein but which comprises at least the thyroid hormone-like compound. For example, and in a preferred embodiment, the foetal-like cardiomyocytes may be first exposed to a culture medium as disclosed herein, but without any thyroid hormone-like compound, followed by replacement of the medium, for example after 1, 2, 3, 4, 5, 6 or 7 days of incubation, with the medium as disclosed herein but which comprises at least one thyroid hormone-like compound for maturing foetal-like cardiomyocytes derived from PESC and/or iPSC in in vitro culture.

Methods of the Invention

In a second aspect, the invention relates to a method to generate adult-like cardiomyocytes from PESC and/or iPSC, in particular from foetal-like cardiomyocytes differentiated from said PESC and/or iPSC, comprising the steps of:
  (a) providing the one or more foetal-like cardiomyocytes derived from PESC and/or iPSC;
  (b) contacting said foetal-like cardiomyocytes with the culture medium composition as taught herein so as to allow maturation of said foetal-like cardiomyocytes into adult-like cardiomyocytes.

In step (a), the foetal-like (immature) cardiomyocytes may be obtained from PESC and/or iPSC in in vitro culture or can be obtained from other sources such as commercially available cell lines. The skilled person knows how to obtain as well as how to culture said foetal-like (immature) cardiomyocytes so that they are suitable for use in the method of the invention.

In an embodiment, the foetal-like (immature) cardiomyocytes may be from mammalian origin, for instance from a mouse, rat, horse, dog, cow, or non-human primate and the like. In a preferred embodiment, the foetal-like (immature) cardiomyocytes may be from human origin, for example as obtained by techniques like the technique described in Chung (Chung et al (2008) Cell Stem Cell, Vol 2(2):113-117).

In step (b), the term 'contacting' as used herein refers to a direct interaction between the culture medium compositions as taught herein and cells (e.g. cardiomyocytes) or a cell culture (e.g. cardiomyocyte culture).

In one embodiment, the foetal-like cardiomyocytes of step (b) are in contact with the culture medium composition as taught herein for at least about 1 day up to about 4 weeks.

In an embodiment, the foetal-like cardiomyocytes of step (b) are in contact with the culture medium composition as taught herein for at least about 1 day, preferably about 2 days, preferably about 3 days, preferably about 4 days, preferably about 5 days, preferably about 6 days, preferably about 7 days, preferably about 8 days, preferably about 9 days, preferably about 10 days, preferably about 11 days, preferably about 12 days, preferably about 13 days, preferably about 14 days, more preferably about 15 days.

In an embodiment, the foetal-like cardiomyocytes of step (b) are in contact with the culture medium composition as taught herein for at least about 3 days up to about 15 days.

In a preferred embodiment, the foetal-like cardiomyocytes of step (b) are in contact with the culture medium composition as taught herein for about 15 days.

In an embodiment, the foetal-like cardiomyocytes of step (b) are first in contact with the culture medium composition as taught herein but which lacks a/the thyroid hormone-like compound for a period of, for example, between 1 and 10 days, for example 1, 2, 3, 4, 5, 6, or 7 days, prior to be in contact with the culture medium composition as taught herein and which comprises at least one thyroid hormone-like compound. For instance, the foetal-like cardiomyocytes of step (b) can be incubated in the culture medium composition as taught but devoid of any a thyroid hormone-like for a period of 2 days, followed by replacing the culture medium composition by a culture medium composition as taught herein but comprising at least one thyroid hormone like compound (e.g. T3), and allow said foetal-like cardiomyocytes to be in contact with the culture medium composition as taught herein but comprising at least one thyroid hormone-like compound for the reminder of the treatment, for instance from day 3 to day 4, or from day 3 to day 5, or from day 3 to day 6, or from day 3 to day 7, or from day 3 to day 8, or from day 3 to day 9, or from day 3 to day 10, or from day 3 to day 11, or from day 3 to day 12, or from day 3 to day 13, or from day 3 to day 14 or from day 3 to day 15. In other words, one may start the process of maturation using the method as taught herein using a culture medium composition devoid of any thyroid hormone-like compound while continuing afterwards a culture medium composition as taught herein which comprises at least one thyroid hormone-like compound.

The present inventor found that it may be advantageous to first contact the foetal-like cardiomyocytes derived from PESC and/or iPSC in in vitro culture with the culture medium composition of the invention as taught herein but lacking a/the thyroid hormone-like compound prior contact with the culture medium composition of the invention as taught herein but comprising at least one thyroid hormone-like compound so as to improve or facilitate the formation of a monolayer of cardiomyocytes in in vitro culture.

In another embodiment, the foetal-like cardiomyocytes that were obtained by differentiating (undifferentiated) PESC and/or iPSC into the cardiomyocytes are cultured under conditions of increasing amounts of thyroid hormone-like compound, for example T3. In other words, in time, the concentration of the thyroid hormone-like compound is increased (either by addition to the medium or by replacement of the medium with new medium as disclosed herein, but with an increased concentration of T3 as compared to the previous medium). For example, the foetal-like cardiomyocytes that were obtained by differentiating (undifferentiated) PESC and/or iPSC may first be cultured on medium as disclosed herein but that is devoid of any thyroid hormone-like compound, for, for example 1, 2, 3 or 4 days (or more). After the 1, 2, 3, or 4 days (or more) the medium is replaced by the culture medium of the current invention with, for example, 10 ng/ml T3 and cultured for an additional 1, 2, 3, or 4 days (or more). Next the medium is replaced with fresh medium according to the current invention and that comprises an increased concentration of thyroid hormone-like compound, for example T3. For example, the culture medium composition in the next step comprises 50 ng/ml of T3. If so desired or required, additional steps with the same concentration of higher concentrations of the thyroid hormone-like compound may be applied in the culturing of the cells, for any number of days desirable.

In one embodiment, the foetal-like cardiomyocytes of step (b) are in contact with the culture medium composition as taught herein, wherein the culture medium composition is at a temperature of at least 21° C. up to a temperature that is not substantially higher than 37° C.

In another embodiment, the foetal-like cardiomyocytes of step (b) are in contact with the culture medium composition as taught herein, wherein the culture medium composition is at a temperature of about 30° C., preferably about 31° C., preferably about 32° C. to about 33° C., preferably about 34° C., preferably about 35° C., preferably about 36° C., more preferably about 37° C. In preferred embodiment, the foetal-like cardiomyocytes of step (b) are in contact with the culture medium composition as taught herein, wherein the culture medium composition is at a temperature of about 37° C.

In one embodiment, the culture medium composition as taught herein is replenished on a daily basis over the duration of the treatment as taught herein.

In a preferred embodiment, the culture medium composition as taught herein is replenished every 2 days or 3 days over the duration of the treatment as taught herein. In an embodiment, the culture medium composition of step (b) is in a solid form, preferably a powder form, that can be dissolved in an aqueous solution so as to obtain the liquid culture medium of steps (b).

In one embodiment, the maturity of adult-like (mature) cardiomyocytes generated from foetal-like (immature) cardiomyocytes derived from PESC and/or iPSC in in vitro culture may be determined by assessing the morphological features of said adult-like cardiomyocytes and comparing the results with that of adult cardiomyocytes obtained from an adult subject (or other sources, e.g. cell lines) as well as with that of foetal-like (immature) cardiomyocytes derived from PESC and/or iPSC in in vitro culture, which were exposed to the culture medium composition as taught herein, which lacks the at least one thyroid hormone-like compound. Methods to assess the morphological features (e.g. shape) and/or histological features (e.g. presence of certain structures or cellular components, organization of the cytoskeleton, etc.) of cells (e.g. cardiomyocytes) so as to obtain information about the morphology and appearance of a given cell are well known in the art. For instance in the present invention, immunohistochemistry techniques may be used to detect or reveal particular cell markers or cytoskeleton markers of cardiac cells. A representative non-limiting example of such marker is alpha-actinin. Other non-limiting examples of markers include troponin C, troponin I, troponin T, myosin heavy chain 6, myosin heavy chain 7, mybpc3, myosin light chain, tropomyosin, titin, myomesin, and the like.

The present inventor found that foetal-like (immature) cardiomyocytes exposed to the culture medium composition as taught herein, which comprises at least one thyroid hormone-like compound, matured into adult-like cardiomyocytes as evidenced by changes in their morphological features that were reminiscent of an adult (or adult-like) stage such as polarization of cells, improved sarcomeric organization, and elongated shape. Such changes in morphological features were less observed in foetal-like (immature) cardiomyocytes that were not exposed to at least one thyroid hormone-like compound during the maturation process in in vitro culture.

In another embodiment, the maturity of adult-like (mature) cardiomyocytes generated from foetal-like (Immature) cardiomyocytes derived from PESC and/or iPSC in in vitro culture by the method as taught herein may be determined by assessing the functional properties of said adult-like cardiomyocytes and comparing the results with that of adult cardiomyocytes obtained from an adult subject (or other sources, e.g. cell line) as well as with that of foetal-like (immature) cardiomyocytes derived from PESC and/or iPSC in in vitro culture, which were exposed to the culture medium composition as taught herein but which lacked at least one thyroid hormone-like compound. Methods to assess the functional properties of cells (e.g. cardiomyocytes) so as to obtain information about functional phenotype a given cell are well known in the art. For instance in the present invention, electrophysiology techniques (among other techniques) may be used to detect or reveal particular function(s) or functional phenotype(s) of a cell (e.g. cardiomyocytes). A non-limiting example of such electrophysiology technique is the so-called 'patch clamp' technique.

The patch clamp technique is a well-known laboratory technique that allows the study of single or multiple ion channels in cells. The technique can be applied to a wide variety of cells, but is especially useful in the study of excitable cells such as neurons, cardiomyocytes, muscle fibers and pancreatic beta cells. In the present invention, such technique can be used to study the properties of the so-called 'action potential', which serves as an indication of the ability of a cell (e.g. cardiomyocytes) to convey an electrical impulse from one cell to another. For instance information about the maximal upstroke velocity, action potential duration, resting membrane potential and amplitude of the action potential can be obtained by using patch clamp technique.

The present inventor found that foetal-like (immature) cardiomyocytes exposed to the culture medium composition as taught herein, which comprises at least one thyroid hormone-like compound, matured into adult-like cardiomyocytes as evidenced by changes in their electrophysiological features which were reminiscent of an adult (or adult-like) stage such as increased maximum upstroke velocity, lower resting membrane potential and increased amplitude of the action potential. Such changes in electrophysiological properties were less observed in foetal-like (immature) cardiomyocytes that were not exposed to at least one thyroid hormone-like compound during the maturation process in in vitro culture.

In a further embodiment, the maturity of adult-like (mature) cardiomyocytes generated from foetal-like (immature) cardiomyocytes derived from PESC and/or iPSC in in vitro culture may be determined by assessing the metabolic profile of said adult-like cardiomyocytes and comparing the results with that of adult cardiomyocytes obtained from an adult subject (or other sources, e.g. cell line) as well as with that of foetal-like (immature) cardiomyocytes derived from PESC and/or iPSC in in vitro culture, which were exposed to the culture medium composition as taught herein but which lacked at least one thyroid hormone-like compound. Methods to assess the metabolic profile of cells (e.g. cardiomyocytes) so as to obtain information about the efficiency and maturity of metabolic function(s) or pathway(s) of a given cell are well known in the art. For instance in the present invention, a so-called 'TMRM assay' may be used to detect or reveal the level of mitochondrial activity in a given cell (e.g. cardiomyocytes). The skilled person is familiar with the TMRM assay and knows how to carry such assay so as to obtain information about the level of mitochondrial activity of cardiomyocytes in in vitro culture.

The present inventor found that foetal-like (immature) cardiomyocytes exposed to the culture medium composition as taught herein, which comprises at least one thyroid hormone-like compound, matured into adult-like cardiomyocytes as evidenced by changes in their metabolic profile which were reminiscent of an adult (or adult-like) stage such as increased mitochondrial activity. Such changes in metabolic profile were observed to a lesser extent in foetal-like (immature) cardiomyocytes that were not exposed to at least one thyroid hormone-like compound during the maturation process in in vitro culture.

In yet another embodiment, the maturity of adult-like (mature) cardiomyocytes generated from foetal-like (immature) cardiomyocytes derived from PESC and/or iPSC in in vitro culture may be determined by assessing the gene expression profile of said adult-like cardiomyocytes and comparing the results with that of adult cardiomyocytes obtained from an adult subject (or other sources, e.g. cell line) as well as with that of foetal-like (immature) cardiomyocytes derived from PESC and/or iPSC in in vitro culture, which were exposed to the culture medium composition as taught herein but which lacked at least one thyroid hormone-like compound. Methods to assess gene expression profile of cells (e.g. cardiomyocytes) so as to obtain information about the presence (absence) of a given gene marker(s) as well as to obtain information about levels of expression of a given gene marker(s) for a given cell (e.g. cardiomyocytes) are well-known in the art. For instance in the present invention, in situ hybridization techniques and/or the so-called 'gene chip' assays may be used detect and/or measure levels of expression of gene markers specific to certain developmental stages (e.g. foetal and adult stages). For instance in the present invention, gene markers indicative of an adult or adult-like stage can be used to establish whether a foetal-like (immature) cardiomyocytes derived from PESC and/or iPSC in in vitro culture and exposed to the culture medium composition as taught herein comprising at least one thyroid hormone-like compound has matured into an adult-like (mature) cardiomyocytes. Non-limiting examples of gene markers indicative of an adult (or adult-like) stage include myosin light chain 2V, calsequestrin and ryanodine receptor and others. Increased (gene) expression of one or more of said adult-like (mature) markers would be indicative of an adult-like (mature) state.

Gene markers indicative of a foetal-like (immature) stage can also be used to establish whether a foetal-like (immature) cardiomyocyte derived from PESC and/or iPSC in in vitro culture has matured (or not) into an adult-like (mature cardiomyocytes). Typically, foetal-like (immature) cardiomyocytes derived from PESC and/or iPSC in in vitro culture exposed to the culture medium composition as taught herein but which lacks at least one thyroid hormone-like compound would express gene markers indicative of a foetal-like (immature) stage. Non-limiting examples of gene markers indicative of a foetal-like (immature) stage include NPPA, NPPB, smooth muscle actin, and skeletal actin. Decreased (gene) expression of one or more of said foetal (immature) markers would be indicative of an adult-like (mature) state.

In one embodiment, undifferentiated PESC and/or iPSC may be used as starting material for the generation of adult-like cardiomyocytes prior to step (a) of the method as taught herein so as to obtain a suitable amount of foetal-like (immature) cardiomyocytes, which are suitable for use in the method of the invention.

Foetal-like (immature) cardiomyocytes can be obtained from undifferentiated PESC and/or iPSC by exposing said undifferentiated PESC and/or iPSC to a differentiation medium composition suitable to differentiate undifferentiated PESC and/or iPSC into foetal-like (immature) cardiomyocytes. The skilled person is well acquainted with methods and culture medium compositions suitable for differentiating undifferentiated PESC and/or iPSC into foetal-like (immature) cardiomyocytes in in vitro culture. For instance in the present invention, a basic differentiation medium composition suitable to differentiate undifferentiated PESC and/or iPSC into foetal-like (immature) cardiomyocytes is a medium composition that is serum-free, comprises (recombinant) albumin, and ascorbic acid, and may further comprise a lipid mixture, insulin, transferrin and selenium, and one or more trace elements.

In another embodiment, the basic differentiation medium composition as taught herein may further comprise amino acids, bovine serum albumin, glucose, vitamins, antibiotics, monothiolglycerol, glutamine, and growth factor(s) or small molecules (e.g. bone morphogenic protein 4 (BMP4), activin A (ACT-A), stem cell factor (SCF), vascular endothelial growth factor (VEGF)), Chir99021 (GSK3 beta inhibitor)), and other components. The skilled person knows what ingredients or substances (as well as at what dosages) to add to the basic differentiation culture medium as taught herein so that it is suitable to differentiate undifferentiated PESC and/or iPSC into foetal-like (immature) cardiomyocytes, which in turn are suitable for use in the method of the invention.

The present inventor observed that the culture medium composition as taught herein, but which lacks a thyroid hormone-like compound, also lead to the development of several adult-like features as just described above but to a lower extend (less efficient, less robust) than what is achievable using the culture medium composition as taught herein but comprising at least one thyroid hormone-like compound.

In one embodiment, the undifferentiated PESC and/or iPSC may be obtained from commercially available sources such as established cell lines, for instance. The skilled person knows how to obtain as well as how to culture said undifferentiated PESC and/or iPSC so that they are suitable for use in the method of the invention.

In an embodiment the undifferentiated PESC and/or iPSC may be from mammalian origin, for instance from a mouse, rat, horse, dog, cow, non-human primates and the like.

In a preferred embodiment, the undifferentiated PESC and/or iPSC may be from human origin, for example as obtained by the method as described by Chung (Chung et al (2008) Cell Stem Cell, Vol 2(2):113-117).

In one embodiment, the undifferentiated PESC and/or iPSC can be differentiated into foetal-like (immature) cardiomyocytes, which are suitable for use in the method as taught herein, using a technique where the differentiation process is carried out in spin embryonic bodies (EB). The skilled person is familiar with differentiation techniques carried out in spin EB.

In another embodiment, the undifferentiated PESC and/or iPSC can be differentiated into foetal-like (immature) cardiomyocytes, which are suitable for use in the method as taught herein, using a technique where the differentiation process is carried out in monolayer. The skilled person is also familiar with differentiation techniques carried out in mononlayer.

Suitable Use of the Culture Medium Composition of the Invention

In a third aspect, the present invention relates to the suitable uses of the culture medium compositions as taught herein.

In one embodiment, the culture medium compositions as taught herein are suitable for maturing foetal-like (immature) cardiomyocytes derived from PESC and/or iPSC in in vitro culture into adult-like (mature) cardiomyocytes in in vitro culture by the method of the invention.

In an embodiment, the PESC and/or iPSC cells may be obtained from mammalian origin, preferably from human origin. Established PESC lines from mammalian origin, preferably from human origin, can also be used. For instance, various mouse PESC cell lines and human PESC lines are known in the art and conditions for their growth and propagation have been well defined. The skilled person knows how to obtain suitable PESC lines (from human or other mammals), for example by a method like the one described by Chung (Chung et al (2008) Cell Stem Cell, Vol. 2(2): 113-117) or any other methods similar to that of Chung et al (supra).

In another embodiment, iPSC are used. The skilled person knows how to obtain and how to culture iPSC so that they are suitable for use in the method of the invention.

In an embodiment, the iPSC may be from mammalian origin, preferably from human origin.

In an embodiment, the culture medium compositions of the invention may be used to maintain adult-like (mature) cardiomyocytes generated from foetal-like (Immature) cardiomyocytes derived from PESC and/or iPSC in in vitro culture for a prolonged period of time, for instance for 1 day, 2 days, 3 days, 4 days, 5 days, 6 days, 1 weeks, 2 weeks, 3 weeks, 6 weeks, and up to 6 months. The present inventor found that the culture medium compositions as taught herein enhanced survival (i.e. prevent or alleviate cell death) of adult-like (mature) cardiomyocytes generated from foetal-like (immature) cardiomyocytes derived from PESC and/or iPSC in in vitro culture, by the method as taught herein, over time. This effect was also associated with an increased yield (greater amount) of said adult-like cardiomyocytes in in vitro culture by the method of the invention.

In one embodiment, the culture medium compositions as taught herein may be suitable for use in in vitro cell culture in general, preferably in a three-dimensional culture.

In another embodiment, the culture medium compositions as taught herein may be used to boost or increase the survival of adult-like (mature) cardiomyocytes generated from PESC-derived foetal-like (immature) cardiomyocytes and/or iPSC-derived foetal-like (immature) cardiomyocytes in in vitro culture while at the same time promoting maturation of said foetal-like (immature) cardiomyocytes into adult-like (mature) cardiomyocytes. Indeed, the present inventor surprisingly found that the culture medium compositions as taught herein not only promote and improve the maturation of foetal-like (immature) cardiomyocytes derived from PESC and/or iPSC in in vitro culture into adult-like cardiomyocytes but also increase their survival in in vitro culture. This effect was also found to be associated with an increased yield of adult-like (mature) cardiomyocytes in in vitro culture using the method as taught herein.

In a further embodiment, the culture medium compositions as taught herein may be used for transporting adult-like (mature) cardiomyocytes generated from foetal-like (immature) cardiomyocytes derived from PESC and/or iPSC in in vitro culture by the method of the present invention or obtained from other sources. For instance, the culture medium compositions of the present invention may be particularly suitable for transporting said adult-like (mature) cardiomyocytes in containers such as tubes, petri dishes, eppendorfs, flasks, bottles, and the like.

In an embodiment, the adult-like (mature) cardiomyocytes generated from foetal-like (immature) cardiomyocytes derived from PESC and/or iPSC in in vitro culture by the method of the present invention may be used for screening cardiac drugs and other drugs in vitro, for instance in high-throughput screening assays.

In another embodiment, the adult-like (mature) cardiomyocytes generated from foetal-like (immature) cardiomyocytes derived from PESC and/or iPSC in in vitro culture by the method of the present invention may be used in predictive toxicology screen assays.

In a further embodiment, the adult-like (mature) generated from foetal-like (immature) cardiomyocytes derived from PESC and/or iPSC in in vitro culture by the method of the present invention may be used in cardiovascular research.

In yet another embodiment, the adult-like (mature) cardiomyocytes generated from foetal-like (immature) cardiomyocytes derived from PESC and/or iPSC in in vitro culture by the method of the present invention may be used for the treatment of cardiac diseases or other diseases as well as for the treatment of cardiac tissue damage or cardiac injuries in a subject in need thereof or subjects which are at risk of developing cardiovascular diseases or disorders and/or suffer cardiac tissue damage or injuries.

In an embodiment of the invention, the subject may be a mammal such as a non-human primate, dog, cat, cow, mouse, rat, horse and the like.

In a preferred embodiment, the subject may be a human subject, preferably an adult human subject.

Non-limiting examples of cardiac diseases and disorders included, but are not limited to, atherosclerosis, stroke, congenital heart disease, congestive heart failure, angina, myocarditis, coronary artery disease, cardiomyopathy, dilated cardiomyopathy, hypertrophic cardiomyopathy, endocarditis, myocardial infarction (heart attack), diastolic dysfunction, cerebrovascular disease, valve disease, high blood pressure (hypertension), mitral valve prolapse and venous thromboembolism. At risk subjects include those with a family history (high blood pressure, heart disease), genetic predisposition (hypercholesterolemia), or who have suffered a previous affliction with a cardiac disease or disorder. At risk subjects further include those with or at risk of high blood pressure or high cholesterol due to a genetic predisposition or a diet, such as high fat, or environmental exposure, such as smokers.

Kits of the Invention

In a fourth aspect, the present invention relates to a kit suitable for generating adult-like cardiomyocytes in in vitro culture comprising the culture medium compositions as taught herein.

In an embodiment, the kit as taught herein may further comprise a culture medium compositions as taught herein but devoid of any thyroid hormone-like compound.

In one embodiment, the culture medium compositions as taught herein, which are comprised in the kit as taught herein may be provided in a liquid form.

In another embodiment, the culture medium compositions as taught herein, which are comprised in the kit as taught herein may be provided in a solid form, preferably a powder form.

In a further embodiment, the kit as taught herein may further comprise (PESC- and/or iPSC-derived, preferably human) foetal-like cardiomyocytes, i.e. the kit may comprise the culture medium composition as disclosed herein comprising at least one thyroid hormone-like compound together with (PESC- and/or iPSC-derived) foetal-like cardiomyocytes or for example the kit may comprise the culture medium composition as disclosed herein comprising at least one thyroid hormone-like compound together with (PESC- and/or iPSC-derived) foetal-like cardiomyocytes together with the culture medium composition as taught herein devoid of any thyroid hormone-like compound.

In one embodiment, the foetal-like (immature) cardiomyocytes may be derived from PESC and/or iPSC and may be from mammalian origin (e.g. rat, mouse, dog, horse, cow, and non-human primate), preferably from human origin.

In an embodiment, the kit as taught herein may further comprise undifferentiated PESC and/or iPSC.

In one embodiment, the undifferentiated PESC and/or iPSC may be obtained from mammalian origin (e.g. rat, mouse, dog, horse, cow, and non-human primate), preferably from human origin.

In another embodiment, the kit as taught herein may comprise instructions on how to generate adult-like cardiomyocytes according to the method of the invention using foetal-like (immature) cardiomyocytes derived from PECS and/or iPSC as starting material.

In another embodiment, the kit as taught herein may comprise instructions on how to generate adult-like cardiomyocytes according to the method of the invention using undifferentiated PESC and/or undifferentiated iPSC as starting material.

For instance, instructions may be provided on how to culture, expend or proliferate, differentiate, maturate, maintain, and/or preserve adult-like (mature) cardiomyocytes in in vitro culture depending on whether the starting material is a foetal-like (immature) cardiomyocyte derived from PESC and/or iPSC or an undifferentiated PESC and/or an undifferentiated iPSC.

In yet another embodiment, the kit as taught herein may further comprise the basic differentiation medium composition as taught herein, which may be used to differentiate undifferentiated PESC and/or undifferentiated iPSC into foetal-like (immature) cardiomyocytes in in vitro culture.

In an embodiment, the components of the kit as taught herein may be supplied in suitable packaging material. The term 'packaging material' as used herein refers to a physical structure housing the components of the kit. The packaging material can maintain the components in a sterile condition, and can be made of material commonly used for such purposes (e.g., paper, glass, plastic, foil, ampoules, etc.). For example, the culture medium compositions as taught herein may be packaged in vials, eppendorfs plastic or glass bottles or any other suitable carriers commonly used for such purposes.

Adult-like (mature) cardiomyocytes obtainable by the method as taught herein, or obtainable form other sources, may be packaged in a tissue culture dish, tube, flask, roller bottles or plates (e.g., a single multi-well plate or dish such as an 8, 16, 32, 64, 96, 384 and 1536 multi-Well plate or dish) or any suitable carriers commonly used for such purposes, and be included in the kit as taught herein as such.

In one embodiment, the kit as taught herein may further comprise additional components such as cell growth medium composition, buffering agents, preservative agents, cell stabilizing agents and the likes.

In an embodiment, each component of the kit as taught herein may be supplied within an individual container or dispenser or may be supplied in a mixture. Further in another embodiment, all of the various containers or dispensers of the kit as taught herein may be supplied within a single or multiple packages, depending on the commercial and non-commercial purposes.

BRIEF DESCRIPTION OF THE FIGURES RELATED TO THE INVENTION

FIG. 1 displays the effects of T3 on the maturation of foetal-like (immature) cardiomyocytes derived from human pluripotent embryonic stem cells (PESCs) in in vitro culture. The maturity of PESC-derived foetal-like (Immature) cardiomyocytes was revealed by their morphological features, which were assessed by immunohistochemistry (immunofluorescence) techniques using an antibody directed against alpha-actinin. Panels A and B show the morphological features of PESC-derived foetal-like (Immature) cardiomyocytes cultured in a basic differentiation medium as taught herein but which lacks T3 (control situation 1). Panels C and D show the morphological features of PESC-derived foetal-like (immature) cardiomyocytes cultured in the culture medium composition (or maturation medium composition) as taught herein but which lacks T3 (control situation 2). Panels E and F show the morphological features of PESC-derived foetal-like (Immature) cardiomyocytes cultured in the culture medium composition of the invention but which comprises 100 ng/ml of T3. Panels B, D, and F represent magnifications of panels A, C, and E, respectively. The results show that compared to the control situations 1 and 2 (see panels A-D), PESC-derived foetal-like (immature) cardiomyocytes cultured in the culture medium composition of the invention comprising T3 (see panels E, and F) displayed morphological features that were the most reminiscent or the closest to an adult cardiomyocyte phenotype, including polarization of cells, improved sarcomeric organization, and elongated shape. Note that in comparison to control 1 (see panels A and B), cardiomyocytes cultured in the culture medium composition as taught herein but lacking T3 (control 2, see panels C and D) also displayed morphological features that were reminiscent of an adult cardiomyocyte phenotype but to a lower extend (less efficient, less robust) than what was observed in the presence of T3 (see panels E and F).

Figure 2:
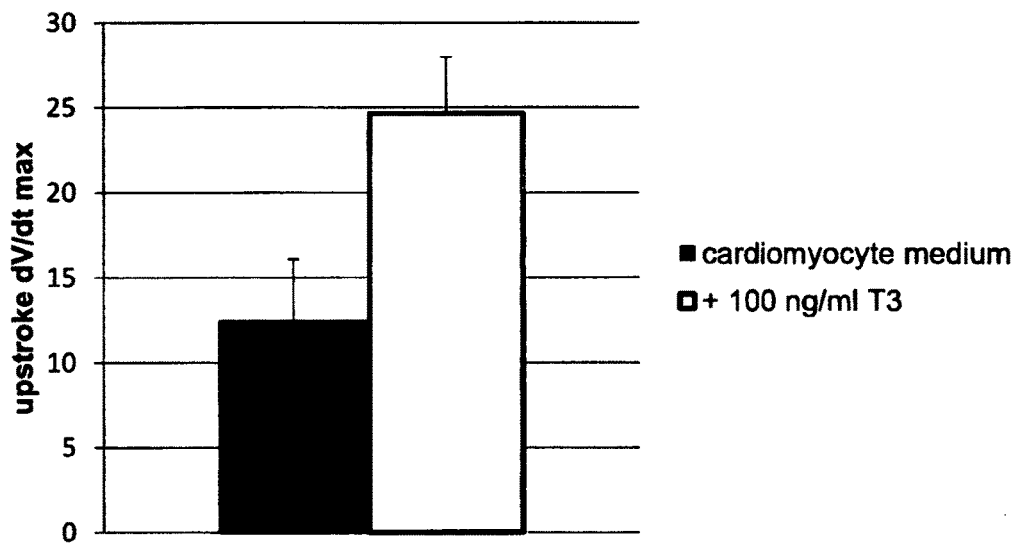
Figure 2:
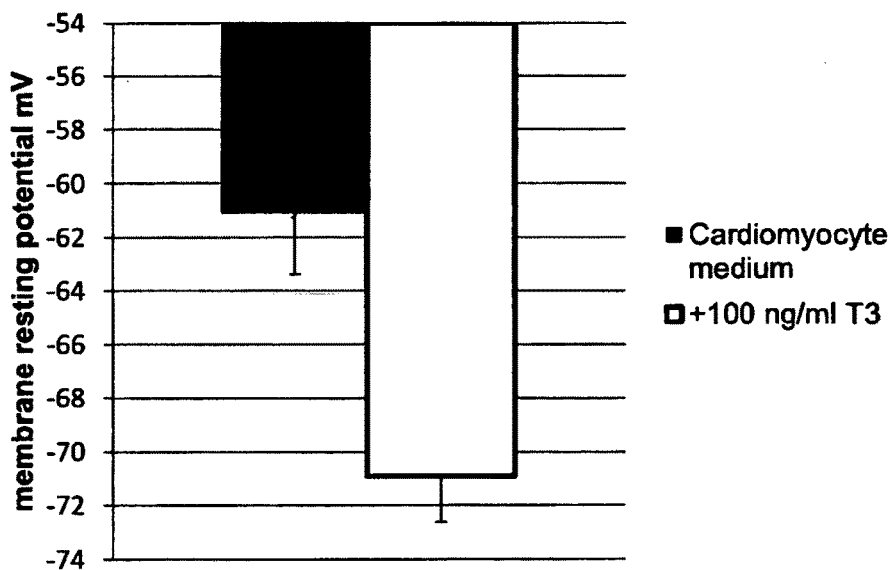
Figure 2:
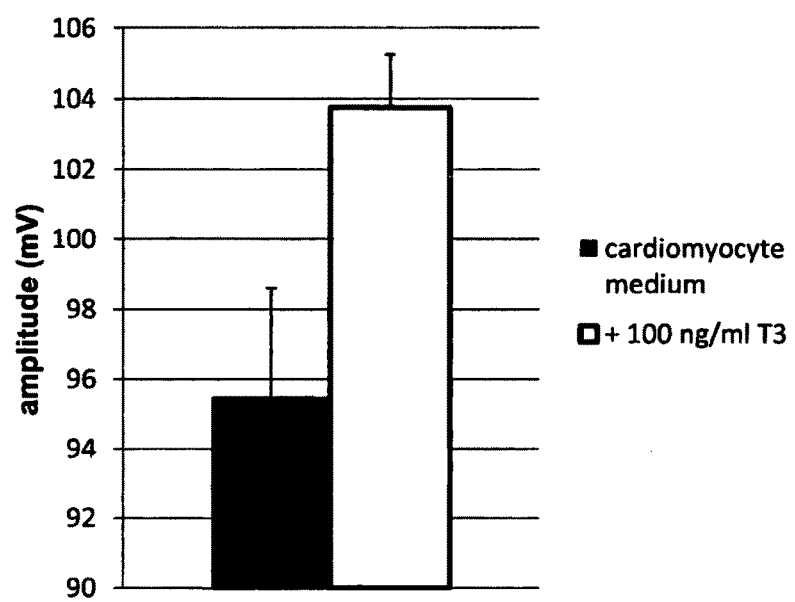

FIG. 2 depicts the effects of T3 on the maturation of foetal-like (immature) cardiomyocytes derived from human pluripotent embryonic stem cells (PESCs) In vitro culture. The maturity of the PESC-derived foetal-like (immature) cardiomyocytes was revealed by their electrophysiological properties, which were assessed by patch clamp techniques. PESC-derived foetal-like (immature) cardiomyocytes were cultured for 12 days either in the culture medium as taught herein which lacks T3 (control situation, see black bar on graphs) or in the culture medium as taught herein which comprises 100 ng/ml of T3 (see white bar on graph). Panel A shows the effects of T3 on the maximal upstroke velocity. Panel B shows the effects of T3 on the resting membrane potential. Panel C shows the effects of T3 on the amplitude of an action potential. The results show that, compared to the control situation, PESC-derived foetal-like (Immature) cardiomyocytes treated with T3 display improvement in several electrophysiological parameters including greater maximal upstroke velocity (see panel A), lower resting membrane potential (see panel B), and greater amplitude of the action potential (see panel C). Data presented as mean+/−SEM.

Figure 3:
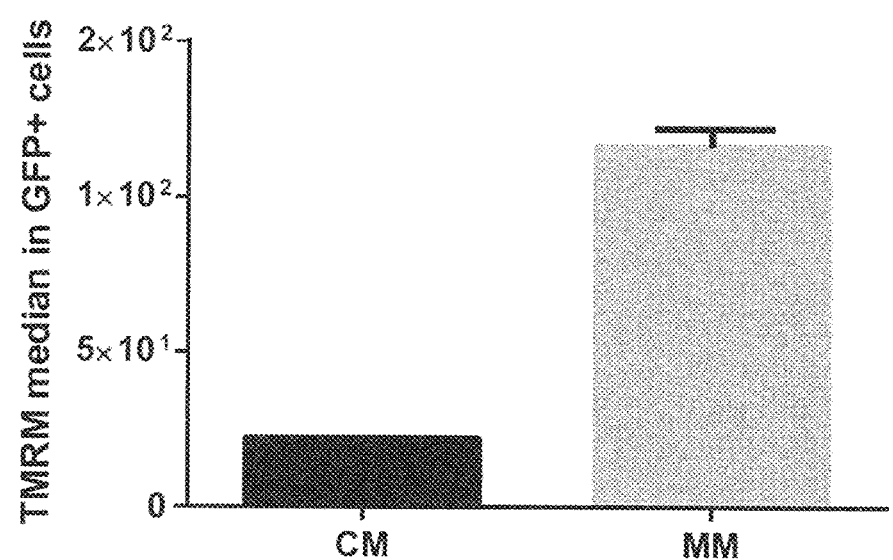

FIG. 3 displays the effects of T3 on the maturation of foetal-like (immature) cardiomyocytes derived from PESC in in vitro culture. The maturity of the PESC-derived foetal-like (Immature) cardiomyocytes was revealed by their metabolic properties, which were assessed using a TMRM assay, which utilizes the potentiometric red fluorescent dye tetramethylrhodamine methyl ester, commonly known as TMRM. Treatment with TMRM results in mitochondrial membrane potential-driven accumulation of TMRM within the inner membrane region of healthy functioning mitochondria. PESC-derived foetal-like (immature) cardiomyocytes were cultured for 17 days in either a culture medium composition (CM) as taught herein, which lacks T3 (control situation) or a culture medium composition (CM) as taught herein (also referred to as maturation medium (MM), which comprises 100 ng/ml of T3. Both treatment groups were subjected to a TMRM assay. The results show that, in comparison to the control situation, PESC-derived foetal-like (immature) cardiomyocytes treated with T3 display greater increased in TMRM-associated orange fluorescence indicating a enhanced mitochondrial activity.

EXAMPLES

The present invention is further illustrated, but not limited, by the following Examples. From the above discussion and these Examples, one skilled in the art can ascertain the essential characteristics of the present invention, and without departing from the teaching and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1. Differentiation in Spin Embryonic Bodies (EBs)

The human PESC (hPESC) or human iPSC (hiPSC) were cultured in stem cell medium on mitotically inactivated mouse fibroblasts and passaged using TrypLE Select (Invitrogen). Stem cell medium contains DMEM/F12 (Gibco, cat. no. 11320-033), 20% (v/v) knockout serum replacement (Gibco, cat. no. 10828-028), 10 mM non-essential aminoacids (Gibco, cat. no. 11140-050), 2 mM L-glutamine (Gibco, cat. no. 25030-081) 2b-mercaptoethanol (Gibco, cat. no. 21985-023), 10 ng/ml human bFGF.

One day before differentiation, cells were passaged onto matrigel coated 6-well plates at a density of 1 million cells/well in stem cell medium.

Cells were differentiated in embryoid bodies (EB). At day 0, cells were collected and re-suspended at 6×104 cells ml-1 In basic differentiation medium (serum-free) as taught herein comprising a lipid mixture (2.2 microgram/ml cholesterol, 0.1 microgram/ml of linoleic acid, 0.1 microgram/ml of linolenic acid, and 0.1 microgram/ml of palmitic acid), insulin (1 mg/L), transferrin (0.55 mg/L), selenium (0.00067 mg/L), trace element mix B as described herein (0.01%), Trace element mix C as described herein (0.1%), 20 ng ml-1 of BMP4 (R&D Systems) and 30 ng ml-1 activin A (R&D Systems), 30 ng ml-1 VEGF (R&D systems), 40 ng ml-1 SCF (R&D systems) and 1.5 µM Chir99021 (Axon medchem). An amount of 50 µl of this mix was placed into each well of a 96-well round-bottom non-adherent plate yielding EBs composed of 3,000 cells. On day 3, 7, 10, 14 and 17, the medium was replaced with differentiation medium without growth factors.

The foetal-like (immature) cardiomyocytes produced by this method are suitable for use in the method of the invention as taught herein, i.e. said foetal-like (Immature) cardiomyocytes may be matured into adult-like (mature) cardiomyocytes using the culture medium composition as well as the methods to generate adult-like (mature) cardiomyocytes as taught herein.

Example 2. Differentiation in Monolayer

The human PESC or human iPSC were cultured in monolayer according to the method described in Dambrot et al (2014), Exp. Cell. Res. (in press) (http://dx.doi.org/10.1016/j.yexcr.2014.05.001). In short, the cells were cultured on Matrigel (BD Biosciences)-coated tissue culture dishes in mTeSR1 according to the manufacturer's protocol (Stem Cell Technologies). To initiate differentiation to cardiomyocytes, the cells were dissociated into small clusters of cells and seeded onto a Matrigel-coated cell culture dish in mTeSR1. Three days later (differentiation day(d) 0), the medium was replaced with low insulin (1 mg/I), (LI)-BPEL medium and supplemented with BMP4 (day 0-day 3), Activin A (day 0-day 3), CHIR99021 (day 0-day 3) and XAV939 (day 3-day 6). From day 6 onward BMP4, Activin A, CHIR99021 and XAV939 were absent from the medium.

The foetal-like (immature) cardiomyocytes produced by this method are suitable for use in the method of the invention as taught herein, i.e. said foetal-like (immature) cardiomyocytes may be matured into adult-like (mature) cardiomyocytes using the culture medium composition as well as the methods to generate adult-like (mature) cardiomyocytes as taught herein.

Example 3. Generation of Adult-Like (Mature) Cardiomyocyte from Foetal-Like (Immature) Cardiomyocytes in In Vitro Culture Tissue culture plastic was coated using Matrigel (Corning) at a concentration of 1/100 in DMEM, for 45 min at room temperature. A single cell suspension coming from dissociated embryoid bodies, dissociated monolayers or (commercially obtained) frozen foetal-like (immature) cardiomyocytes, all derived from PESC and/or iPSC in in vitro culture, were seeded at an appropriate density on matrigel coated tissue culture plastic (e.g. In 20-40 k cells per well of a 96-well plate, e.g. 20-200 k per well of a 12 well plate). On day 1 following plating, the foetal-like (immature) cardiomyocytes were exposed to a culture medium composition of the invention, which consists of a serum-free culture medium composition comprising 50 ng/ml of T3 (Sigma T6397), 2 mM of carnitine, 5 mM of creatine, 5 mM of taurine, 2.2 microgram/ml of cholesterol, 0.1 microgram/ml of linoleic acid, 0.1 microgram/ml of linolenic acid, 0.1 microgram/ml of palmitic acid (lipids, for example, from Gibco 11905), 10 mg/ml of insulin, 5.5 mg/ml of transferrin, 0.0067 mg/ml of selenium (Insulin, transferrin and selenium from e.g. Gibco 51500), 0.01% of trace element mix B (as described herein; Cellgro 99-175-CL), 0.1% of trace element mix C (as described herein; Cellgro 99-176-CL), 0.5 w/w % of antibiotics (penicillin-streptomycin mixture commercially available Gibco (Gibco 12070; 5000 U/ML), 0.05 mg/ml ascorbic acid, 2 mM of Glutamax supplement (i.e.

L-alanyl-L-glutamine dipeptide in 0.85% NaCl, commercially available at Gibco, e.g. Gibco 35050), 0.125 w/w % polyvinylalcohol (PVA), 450 nM of alpha monothiolglycerol (MTG) (commercially available), 025 w/w % BSA (Bovostar BSAS1.0) in 46.5% (w/w) IMDM (Gibco 21056) and 46.5% (w/w) HAM F-12 with glutamax (Gibco 31765). All concentrations are expressed as final concentration in the culture medium composition.

The next day the culture medium composition as taught herein was refreshed. This step was repeated every 2-3 days until day 15.

Alternatively, treatment with the culture medium composition as just described above comprising 50 ng/ml of T3 may be started at either at day 3 or day 7 after plating the foetal-like cardiomyocytes, and continued for the remainder of the experiment, i.e. day 15. In this case, the cells are maintained in the culture medium composition as taught herein but devoid of T3 until the treatment with the culture medium composition as described above comprising 50 ng/ml of T3 is started. Various other media within the context of the media disclosed herein, but with varying concentration of individual components may also be used. Best results were obtained were using media comprised of components in concentrations as specifically disclosed herein.

Example 4. Assessment of the Effects of T3 on Morphological Features

Foetal-like (immature) cardiomyocytes derived from PESC in in vitro culture were divided in two experimental groups. The first group was exposed to a culture medium composition as taught herein but which lacked T3 (control situation). The second group was exposed to a culture medium composition as taught herein but which comprised T3 (100 ng/ml). Both groups were incubated in their respective culture medium composition for 5 days. At the term of the treatment, cardiomyocytes from both experimental groups were fixed in 4% paraformaldehyde, permeabilised with phosphate buffer saline (PBS)/0.1% Triton X-100 (Sigma-Aldrich), and blocked with phosphate buffer saline (PBS)/0.1% Triton X-100 (Sigma-Aldrich) 1% BSA. Samples were incubated 1-hour at room temperature with a primary antibodies specific for the following: alpha-actinin (Eptomics Ab 68167) (at a concentration of 1/400). The primary antibody was detected with either Cy3- or Alexa-Fluor 647-conjugated secondary antibodies (at a concentration of 1/250). Images were captured using either a Leica SP5-STED or a Leica SP5 confocal laser-scanning microscope (Leica Microsystems).

The results are presented in FIG. 1. Specifically, the results show that foetal-like (immature) cardiomyocytes derived from PESC in in vitro culture, which were exposed to the culture medium composition as taught herein comprising T3 (see Panels E and F in FIG. 1), matured more efficiently and more robustly into adult-like cardiomyocytes as evidenced by changes in their morphological features, which were reminiscent of an adult (or adult-like) stage such as polarization of cells, improved sarcomeric organization, and elongated shape. Such changes in morphological features were less clearly observed in foetal-like (immature) cardiomyocytes not exposed to T3 during the maturation process in in vitro culture (see Panels A-D in FIG. 1), showing the importance of T3, in particular T3 in the culture medium composition as detailed herein, in the maturation process in vitro.

Example 5. Assessment of the Effects of T3 on the Electrophysiological Properties Foetal-like (immature) cardiomyocytes derived from PESC in in vitro culture were divided in two experimental groups. The first group was exposed to a culture medium composition as taught herein but which lacked T3 (control situation). The second group was exposed to a culture medium composition as taught herein but which comprised T3 (100 ng/ml). Both groups were incubated in their respective culture medium composition for 12 days. At the term of the treatment, foetal-like (immature) cardiomyocytes from both experimental groups were subjected to a patch clamp procedure.

Patch clamp electrophysiology was performed as described by Bellin, M. et al. EMBO J 32, 3161-3175 (2013)), using minor modifications. Action potentials from small groups of cells (5-10 cells) were measured with the perforated patch clamp technique using an Axopatch 200b amplifier (Molecular Devices) and low resistance patch pipettes (1.5-2.5 MΩ). Data acquisition and analyses of action potentials were performed with pClamp 10 (axon instruments) and custom made software. Action Potentials were corrected for the calculated liquid Junction potential (−15 mV).

Action potentials from spontaneous beating cells were measured at 37±0.20 C using a modified Tyrode's solution containing (in mM): 140 NaCl, 5.4 KCl, 1.8 CaCl2), 1.0 MgCl2, 5.5 glucose, 5.0 HEPES; pH7.2 (NaOH). The pipette solution contained (in mM): 125 K-gluconate, 20 KCl, 5 NaCl, 0.22 amphotericin-B, 10 HEPES; pH 7.2 (KOH). The resting membrane potential (RMP), maximal upstroke velocity (dV/dt max), AP amplitude in mV (APA), and AP duration in milli-seconds (APD) at 20, 50 and 90% repolarization (APD50, and APD90, respectively) were analyzed. Upstroke velocity was calculated from the first derivative of the change in voltage as a function of time. Thus the maximum upstroke velocity (dV/dt max) is equal to the maximum positive value of the first derivative of the action potential. Data from 10 consecutive action potentials were averaged.

The results are shown in FIG. 2. Specifically, the results show that foetal-like (immature) cardiomyocytes derived from PESC in in vitro culture that were exposed to the culture medium composition comprising T3, matured more efficiently and more robustly into adult-like cardiomyocytes as evidenced by changes in their electrophysiological features which were reminiscent of an adult (or adult-like) stage such as increased maximum upstroke velocity (see panel A of FIG. 2), lower resting membrane potential (see panel B of FIG. 2) and increased amplitude of the action potential (see panel C of FIG. 2) in comparison to the data obtained for the foetal-like (immature) cardiomyocytes, which were not exposed to T3 during the maturation process in in vitro culture (see black bars in panels A, B, and C of FIG. 2).

Example 6. Assessment of the Effects of T3 on the Metabolic Profile

Foetal-like (immature) cardiomyocytes derived from PESC in in vitro culture were divided in two experimental groups. The first group was exposed to a culture medium composition as taught herein but which lacked T3 (control situation). The second group was exposed to a culture medium composition as taught herein but which comprised T3 (100 ng/ml). Both groups were incubated in their respective culture medium composition for 17 days. An amount of 5 nM TMRM (Invitrogen) was added in the respective media the day before measurement. Cells were dissociated using 5× Tryple, but with TMRM included in all solutions and also present during measurement. Measurements were performed on a Miltenyi MACSquant VYB flow cytometer.

The results are shown in FIG. 3. Specifically, the results show that foetal-like (immature) cardiomyocytes derived from PESC in in vitro culture that were exposed to the culture medium composition as taught herein comprising T3, matured more efficiently and more robustly into adult-like cardiomyocytes as evidenced by changes in their metabolic profile, which were reminiscent of an adult (or adult-like) stage such as increased mitochondrial activity, and in comparison to foetal-like (Immature) cardiomyocytes that were not exposed to T3 during the maturation process in in vitro culture.

The invention claimed is:

1. A method to generate adult-like cardiomyocytes from fetal-like cardiomyocytes, comprising the steps of:
   (a) providing one or more fetal-like cardiomyocyte(s) differentiated from stem cells;
   (b) contacting said one or more fetal-like cardiomyocytes with a culture medium composition so as to allow maturation of said one or more fetal-like cardiomyocytes into adult-like cardiomyocytes, wherein the culture medium composition comprises:
   a lipid mixture comprising at least cholesterol, linoleic acid, oleic acid and at least one selected from the group consisting of linolenic acid, palmitic acid, arachidonic acid, myristic acid, palmitoleic acid, and stearic acid;
   a taurine compound; and
   a creatine compound.

2. The method of claim 1, wherein the lipid mixture comprises, linolenic acid and palmitic acid.

3. The method of claim 1, wherein the lipid mixture comprises cholesterol, linolenic acid, linoleic acid, palmitic acid, arachidonic acid, myristic acid, oleic acid, palmitoleic acid and stearic acid.

4. The method of claim 1, wherein the lipid mixture comprises about 0.01 µg/ml to about 5 µg/ml of cholesterol.

5. The method of claim 1, wherein the lipid mixture comprises about 0.01 µg/mL to about 20 µg/mL of linoleic acid.

6. The method of claim 1, wherein the lipid mixture comprises about 0.01 µg/mL to about 20 µg/mL of palmitic acid.

7. The method of claim 1, wherein the lipid mixture comprises about 0.01 µg/mL to about 20 µg/mL linolenic acid.

8. The method of claim 1, wherein the culture medium composition further comprises a carnitine compound.

9. The method of claim 8, wherein the culture medium composition comprises about 0.5 mM to about 3.5 mM of carnitine.

10. The method of claim 8, wherein the culture medium composition comprises about 1.5 mM to about 2.25 mM of carnitine.

11. The method of claim 1, wherein the culture medium composition comprises about 2 mM to about 7 mM of taurine.

12. The method of claim 1, wherein the culture medium composition comprises about 1 mM to about 10 mM of creatine.

13. The method of claim 1, wherein the culture medium composition further comprises insulin, transferrin and selenium.

14. The method of claim 13, wherein the culture medium composition comprises about 5 mg/L to about 15 mg/L of insulin, about 3 mg/L to about 8 mg/L of transferrin, and about 0.005 mg/L to about 0.0075 mg/L of selenium.

15. The method of claim 1, wherein the culture medium composition further comprises about 0.01 mg/ml to about 10 mg/ml of polyvinyl alcohol (PVA).

16. The method of claim 1, wherein the culture medium composition is serum-free.

17. The method of claim 1, wherein the culture medium composition further comprises a thyroid hormone-like compound.

18. The method of claim 17, wherein the thyroid hormone-like compound is triiodothyronine (T3).

19. The method according to claim 1, wherein the stem cells comprise pluripotent stem cells, wherein the pluripotent stem cells comprise human embryonic stem cells.

20. The method according to claim 1, wherein the stem cells comprise pluripotent stem cells and wherein the pluripotent stem cells comprise human induced pluripotent stem cells.

21. The method of claim 1, wherein the one or more fetal-like cardiomyocytes are in contact with the culture medium for a period of 2 weeks, 3 weeks, 6 weeks, or up to 6 months.

22. The method according to claim 1, wherein the culture medium composition comprises polyvinylalcohol.

23. The method according to claim 1, wherein the culture medium composition comprises polyvinylalcohol and T3.

24. A method to generate adult-like cardiomyocytes from fetal-like cardiomyocytes, comprising the steps of:
   (a) providing one or more fetal-like cardiomyocyte(s) differentiated from stem cells;
   (b) contacting said one or more fetal-like cardiomyocytes with a culture medium composition so as to allow maturation of said one or more fetal-like cardiomyocytes into adult-like cardiomyocytes, wherein the culture medium composition comprises:
   a lipid mixture at least comprising cholesterol and the fatty acids linolenic acid, linoleic acid and palmitic acid;
   a taurine compound; and
   a creatine compound.

25. The method of claim 24, wherein the lipid mixture comprises about 0.01 mg/ml to about 5 µg/ml of cholesterol.

26. The method of claim 24, wherein the culture medium composition further comprises a carnitine compound.

27. The method of claim 24, wherein the culture medium composition is serum-free.

28. The method of claim 24, wherein the culture medium composition further comprises triiodothyronine (T3).

29. A method to generate adult-like cardiomyocytes from fetal-like cardiomyocytes, comprising the steps of:
   (a) providing one or more fetal-like cardiomyocyte(s) differentiated from stem cells;
   (b) contacting said one or more fetal-like cardiomyocytes with a culture medium composition so as to allow maturation of said one or more fetal-like cardiomyocytes into adult-like cardiomyocytes, wherein the culture medium composition comprises:
   a lipid mixture at least comprising cholesterol;
   a taurine compound; and
   a creatine compound.

30. The method of claim 29, wherein the lipid mixture comprises cholesterol, linolenic acid, linoleic acid, palmitic acid, arachidonic acid, myristic acid, oleic acid, palmitoleic acid and stearic acid.

31. The method of claim 29, wherein the lipid mixture comprises about 0.01 µg/ml to about 5 µg/ml of cholesterol.

32. The method of claim 29, wherein the culture medium composition further comprises a carnitine compound.

33. The method of claim 29, wherein the culture medium composition further comprises triiodothyronine (T3).

34. A method to generate adult-like cardiomyocytes from fetal-like cardiomyocytes, comprising the steps of:
   (a) providing one or more fetal-like cardiomyocyte(s) differentiated from stem cells;
   (b) contacting said one or more fetal-like cardiomyocytes with a culture medium composition so as to allow maturation of said one or more fetal-like cardiomyocytes into adult-like cardiomyocytes, wherein the culture medium composition comprises:
   a lipid mixture;
   a taurine compound;
   a creatine compound; and
   polyvinylalcohol and/or T3.

35. The method of claim 34, wherein the lipid mixture comprises cholesterol, linolenic acid, linoleic acid, palmitic acid, arachidonic acid, myristic acid, oleic acid, palmitoleic acid and stearic acid.

36. The method of claim 34, wherein the lipid mixture comprises about 0.01 µg/ml to about 5 µg/ml of cholesterol.

37. The method of claim 34, wherein the culture medium composition further comprises a carnitine compound.

38. The method of claim 34, wherein the one or more fetal-like cardiomyocytes are in contact with the culture medium for a period of 2 weeks, 3 weeks, 6 weeks, or up to 6 months.

39. A method to generate adult-like cardiomyocytes from fetal-like cardiomyocytes, comprising the steps of:
   (a) providing one or more fetal-like cardiomyocyte(s) differentiated from stem cells;
   (b) contacting said one or more fetal-like cardiomyocytes with a culture medium composition so as to allow maturation of said one or more fetal-like cardiomyocytes into adult-like cardiomyocytes, wherein the culture medium composition comprises:
   a lipid mixture;
   a taurine compound;
   a creatine compound; and
   polyvinylalcohol and/or T3,
   wherein the lipid mixture at least comprises cholesterol and the fatty acids linolenic acid, linoleic acid and palmitic acid.

40. The method of claim 39, wherein the lipid mixture comprises about 0.01 µg/ml to about 5 µg/ml of cholesterol.

41. The method of claim 39, wherein the culture medium composition further comprises a carnitine compound.

42. The method of claim 39, wherein the culture medium composition is serum-free.

43. The method of claim 39, wherein the one or more fetal-like cardiomyocytes are in contact with the culture medium for a period of 2 weeks, 3 weeks, 6 weeks, or up to 6 months.

\* \* \* \* \*